US008198426B2

(12) United States Patent
Paonessa et al.

(10) Patent No.: US 8,198,426 B2
(45) Date of Patent: Jun. 12, 2012

(54) HEPATITIS C VIRUS REPLICONS AND REPLICON ENHANCED CELLS

(75) Inventors: Giacomo Paonessa, Rome (IT); Giovanni Migliaccio, Rome (IT); Raffaele De Francesco, Rome (IT)

(73) Assignee: Istituto di Ricerche di Biologia Molecolare P. Angeletti S.p.A., Rome (IT)

( * ) Notice: Subject to any disclaimer, the term of this patent is extended or adjusted under 35 U.S.C. 154(b) by 2095 days.

(21) Appl. No.: 10/467,000

(22) PCT Filed: Jan. 16, 2002

(86) PCT No.: PCT/EP02/00526
§ 371 (c)(1),
(2), (4) Date: Jul. 21, 2003

(87) PCT Pub. No.: WO02/059321
PCT Pub. Date: Aug. 1, 2002

(65) Prior Publication Data
US 2004/0067486 A1 Apr. 8, 2004

Related U.S. Application Data

(60) Provisional application No. 60/263,479, filed on Jan. 23, 2001.

(51) Int. Cl.
*C07H 21/00* (2006.01)
*C07H 21/04* (2006.01)
*C12N 7/00* (2006.01)
*C12N 15/00* (2006.01)

(52) U.S. Cl. .................. 536/23.72; 536/23.7; 435/235.1; 435/320.1

(58) Field of Classification Search ............... 536/23.72, 536/23.7; 435/320.1, 69.1, 69.5, 70.1, 235.1, 435/239, 325, 366, 367, 455
See application file for complete search history.

(56) References Cited

U.S. PATENT DOCUMENTS

| 5,739,002 | A | 4/1998 | De Francesco et al. | |
|---|---|---|---|---|
| 6,630,343 | B1 * | 10/2003 | Bartenschlager | 435/320.1 |
| 6,930,095 | B2 * | 8/2005 | Bichko | 514/44 |
| 7,049,428 | B1 * | 5/2006 | Rice et al. | 536/23.72 |
| 2002/0064771 | A1 * | 5/2002 | Zhong et al. | 435/5 |
| 2002/0098202 | A1 | 7/2002 | Wimmer et al. | |
| 2002/0111313 | A1 | 8/2002 | Campbell et al. | |
| 2002/0142350 | A1 | 10/2002 | Kukolj et al. | |
| 2002/0142455 | A1 | 10/2002 | Selby et al. | |
| 2002/0147160 | A1 | 10/2002 | Bhat et al. | |
| 2002/0155582 | A1 * | 10/2002 | Lemon et al. | 435/235.1 |

FOREIGN PATENT DOCUMENTS

| EP | 1 043 399 A2 | 10/2000 |
|---|---|---|
| WO | WO 96/37619 | 11/1996 |
| WO | WO 01/89364 | 11/2001 |
| WO | WO 02/38793 | 5/2002 |
| WO | WO 02/057287 | 7/2002 |
| WO | WO 02/057425 | 7/2002 |
| WO | WO 02/094796 | 11/2002 |

OTHER PUBLICATIONS

Frese et al Journal of General Virology (2001), 82, 723-733.*
Gu et al J Virol. 2003; 77(9): 5352-9.*
Verma and Somia (1997) Nature 389:239-242.*
Pfeifer and Verma (2001) Annual Review of Genomics and Human Genetics.2: 177-211.*
Grobler Journal of Biological Chemistry, 2003, 278, 16741-16746.*
Lanford et al Virology, 2002, 293, 1-9.*
Krieger et al J. Virology, 2001, 75(10), 4614-4624.*
Kunkel, Proc. Natl. Acad. Sci. 1986, 82, 488-492.*
NCBI Accession No. P16493, GI 138337 Aug. 1, 1990.*
NCBI accession No. AC003959, Dec. 30, 1997.*
Miller et al FASEB J. 1995; 9(2): 190-199.*
Ngo et al., 1994, The protein Folding Problem and Tertiary Structure Prediction, pp. 491-495.*
Guo et al Journal of Virology, 2001, 8516-8523.*
Nelson et al., Journal of Virology, 2006, 80, 3, 1181-1190.*
Murray et al Journal of Virology, 2003, 77(5), 2928-2935.*
Tanji et al Journal of Virology, 1995, 3980-3986.*
Bartenschlager, R. et al. "Nonstructural Protein 3 of the Hepatitis C Virus Encodes a Serine-Type Proteinase Required for Cleavage at the NS3/4 and NS4/5 Junctions", Journal of Virology, 1993, vol. 67, pp. 3835-3844.
Behrens, S. et al. "Identification and properties of the RNA-dependent RNA polymerase of hepatitis C virus", The EMBO Journal, 1996, vol. 15, pp. 12-22.
Blight, K. et al. "Efficient Initiation of HCV RNA Replication in Cell Culture", Science, 2000, vol. 290, pp. 1972-1974.
Choo, Q. et al. "Isolation of a cDNA Clone Derived from a Blood-Borne Non-A, Non-B Viral Hepatitis Genome", Science, 1989, vol. 244, pp. 359-262.
De Francesco, R. et al. "Biochemical and Immunological Properties of the Nonstructural Proteins of the Hepatitis C Virus: Implications for Development of Antiviral Agents and Vaccines", Seminars in Liver Disease, 2000, vol. 20, pp. 69-83.
Failla, C. et al. "Both NS3 and NS4A are Required for Proteolytic Processing of Hepatitis C Virus Nonstructural Proteins", Journal of Virology, 1994, vol. 68, pp. 3753-3760.
Grakoui, A. et al. "A second hepatitis C virus-encoded proteinase", Proc. Natl. Acad. Sci. USA, 1993, vol. 90, pp. 10583-10587.
Grakoui, A. et al. "Expression and Identification of Hepatitis C Virus Polyprotein Cleavage Products", Journal of Virology, 1993, vol. 67, pp. 1385-1395.
Hijikata, M. et al. "Proteolytic processing and membrane association of putative nonstructural proteins of hepatitis C virus", Proc. Natl. Acad. Sci. USA, 1993, vol. 90, pp. 10773-10777.
Honda, M. et al. "Structural Requirements for Initiation of Translation by Internal Ribosome Entry within Genome-Length Hepatitis C Virus RNA", Virology, 1996, vol. 222, pp. 31-42.

(Continued)

*Primary Examiner* — Anoop Singh
(74) *Attorney, Agent, or Firm* — Melissa B. Wenk; Sheldon O. Heber

(57) ABSTRACT

The present invention features nucleic acid containing one or more adaptive mutations, and HCV replicon enhanced cells. Adaptive mutations are mutations that enhance HCV replicon activity. HCV replicon enhanced cells are cells having an increased ability to maintain an HCV replicon.

6 Claims, No Drawings

OTHER PUBLICATIONS

Kolykhalov, A. et al. "Hepatitis C Virus-Encoded Enzymatic Activities and Conserved RNA Elements in the 3' Nontranslated Region Are Essential for Virus Replication in Vivo", Journal of Virology, 2000, vol. 74, pp. 2046-2051.

Kolykhalov, A. et al. "Identification of a Highly Conserved Sequence Element at the 3' Terminus of Hepatitis C Virus Genome RNA", Journal of Virology, 1996, vol. 70, pp. 3363-3371.

Kuo, G. et al. "An Assay for Circulating Antibodies to a Major Etiologic Virus of Human Non-A, Non-B Hepatitis", Science, 1989, vol. 244, pp. 362-364.

Llinas-Brunet, M. et al. "High Potent and Selective Peptide-Based Inhibitors of the Hepatitis C Virus Serine Protease: Towards Smaller Inhibitors", Bioorganic & Medicinal Chemistry Letters, 2000, vol. 10, pp. 2267-2270.

Lohmann, V. et al. "Biochemical and Kinetic Analyses of NS5B RNA-Dependent RNA Polymerase of the Hepatitis C Virus", Virology, 1998, vol. 249, pp. 108-118.

Lohmann, V. et al. "Mutations in Hepatitis C Virus RNAs Conferring Cell Culture Adaptation", Journal of Virology, 2001, vol. 75, pp. 1437-1449 (The mailing date of the Feb.-1 (#3) 2001 issue of the Journal of Virology was Jan. 9, 2001. The full text was posted on the Internet on Jan. 10, 2001.).

Lohmann, V. et al. "Replication of Subgenomic Hepatitis C Virus RNAs in a Hepatoma Cell Line", Science, 1999, vol. 285, pp. 110-113.

Mizushima, H. et al. "Analysis of N-Terminal Processing of Hepatitis C Virus Nonstructural Protein 2", Journal of Virology, 1994, vol. 68, pp. 2731-2734.

Pawlotsky, J. "Hepatitis C virus (HCV) NS5A protein: role in HCV replication and resistance to interferon-a", Journal of Viral Hepatitis, 1999, vol. 6, Suppl. 1, pp. 47-48.

Pietschmann, T. et al. "Characterization of Cell Lines Carrying Self-Replicating Hepatitis C Virus RNAs", Journal of Virology, 2001, vol. 75, pp. 1252-1264 (The mailing date of the Feb.-1 (#3) 2001 issue of the Journal of Virology was Jan. 9, 2001. The full text was posted on the Internet on Jan. 10, 2001.).

Takamizawa, A. et al. "Structure and Organization of the Hepatitis C Virus Genome Isloated from Human Carriers", Journal of Virology, 1991, vol. 65, pp. 1105-1113.

Tanaka, T. et al. "Structure of the 3' Terminus of the Hepatitis C Virus Genome", Journal of Virology, 1996, vol. 70, pp. 3307-3312.

Tomei, L. et al. "NS3 Is a Serine Protease Required for Processing of Hepatitis C Virus Polyprotein", Journal of Virology, 1993, vol. 67, pp. 4017-4026.

Yoo, B. et al. "Transfection of a Differentiated Human Hepatoma Cell Line (Huh7) with In Vitro-Transcribed Hepatitis C Virus (HCV) RNA and Establishment of a Long-Term Culture Persistently Infected with HCV", Journal of Virology, 1995, vol. 69, pp. 32-38.

Genebank Accession No. AF207768, Apr. 27, 2000.

Genebank Accession No. AAR68864, Dec. 6, 1995.

Genebank Accession No. AJ242652, May 11, 2000.

Patent Abstracts of Japan, vol. 1995, No. 2, 1995.

Graziani, R. et al. "Dominant negative effect of wild-type NS5A on NS5A-adapted subgenomic hepatitis C virus RNA replicon", Journal of General Virology, 2004, vol. 85, pp. 1867-1875.

Murray, E. et al. "Persistent Replication of Hepatitis C Virus Replicons Expressing the B-Lactamase Reporter in Subpopulations of Highly Permissive Huh7 Cells", Journal of Virology, 2003, vol. 77, pp. 2928-2935.

Zuck, P. et al. "A cell-based B-lactamase reporter gene assay for the identification of inhibitors of hepatitis C virus replication", Analytical Biochemistry, 2004, vol. 334, pp. 344-355.

* cited by examiner

SEQUENCE LISTING

```
<160> NUMBER OF SEQ ID NOS: 13

<210> SEQ ID NO 1
<211> LENGTH: 3010
<212> TYPE: PRT
<213> ORGANISM: Con 1 HCV isolate nucleic acid

<400> SEQUENCE: 1

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Val Tyr His Val Thr Asn Asp Cys Ser
        195                 200                 205

Asn Ala Ser Ile Val Tyr Glu Ala Ala Asp Met Ile Met His Thr Pro
    210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Ala Ala Ala Leu Cys
            260                 265                 270

Ser Ala Met Tyr Val Gly Asp Leu Cys Gly Ser Val Phe Leu Val Ala
        275                 280                 285
```

-continued

```
Gln Leu Phe Thr Phe Ser Pro Arg Arg His Glu Thr Val Gln Asp Cys
    290                 295                 300

Asn Cys Ser Ile Tyr Pro Gly His Val Thr Gly His Arg Met Ala Trp
305                 310                 315                 320

Asp Met Met Met Asn Trp Ser Pro Thr Ala Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly Gly
    370                 375                 380

Thr Tyr Val Thr Gly Gly Thr Met Ala Lys Asn Thr Leu Gly Ile Thr
385                 390                 395                 400

Ser Leu Phe Ser Pro Gly Ser Ser Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu Asn Thr Gly Phe Leu Ala Ala Leu Phe Tyr Val His Lys Phe Asn
        435                 440                 445

Ser Ser Gly Cys Pro Glu Arg Met Ala Ser Cys Ser Pro Ile Asp Ala
    450                 455                 460

Phe Ala Gln Gly Trp Gly Pro Ile Thr Tyr Asn Glu Ser His Ser Ser
465                 470                 475                 480

Asp Gln Arg Pro Tyr Cys Trp His Tyr Ala Pro Arg Pro Cys Gly Ile
                485                 490                 495

Val Pro Ala Ala Gln Val Cys Gly Pro Val Tyr Cys Phe Thr Pro Ser
            500                 505                 510

Pro Val Val Gly Thr Thr Asp Arg Phe Gly Val Pro Thr Tyr Ser
        515                 520                 525

Trp Gly Glu Asn Glu Thr Asp Val Leu Leu Leu Asn Asn Thr Arg Pro
    530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Ile Gly Asn
                565                 570                 575

Lys Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
        595                 600                 605

Val His Tyr Pro Tyr Arg Leu Trp His Tyr Pro Cys Thr Val Asn Phe
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asn Leu Glu Asp
                645                 650                 655

Arg Asp Arg Ser Glu Leu Ser Pro Leu Leu Leu Ser Thr Thr Glu Trp
            660                 665                 670

Gln Val Leu Pro Cys Ser Phe Thr Thr Leu Pro Ala Leu Ser Thr Gly
        675                 680                 685

Leu Ile His Leu His Gln Asn Val Val Asp Val Gln Tyr Leu Tyr Gly
    690                 695                 700

Ile Gly Ser Ala Val Val Ser Phe Ala Ile Lys Trp Glu Tyr Val Leu
705                 710                 715                 720
```

-continued

Leu Leu Phe Leu Leu Leu Ala Asp Ala Arg Val Cys Ala Cys Leu Trp
              725                 730                 735

Met Met Leu Leu Ile Ala Gln Ala Glu Ala Ala Leu Glu Asn Leu Val
              740                 745                 750

Val Leu Asn Ala Ala Ser Val Ala Gly Ala His Gly Ile Leu Ser Phe
              755                 760                 765

Leu Val Phe Phe Cys Ala Ala Trp Tyr Ile Lys Gly Arg Leu Val Pro
              770                 775                 780

Gly Ala Ala Tyr Ala Leu Tyr Gly Val Trp Pro Leu Leu Leu Leu
785               790                 795                 800

Leu Ala Leu Pro Pro Arg Ala Tyr Ala Met Asp Arg Glu Met Ala Ala
              805                 810                 815

Ser Cys Gly Gly Ala Val Phe Val Gly Leu Ile Leu Leu Thr Leu Ser
              820                 825                 830

Pro His Tyr Lys Leu Phe Leu Ala Arg Leu Ile Trp Trp Leu Gln Tyr
              835                 840                 845

Phe Ile Thr Arg Ala Glu Ala His Leu Gln Val Trp Ile Pro Pro Leu
              850                 855                 860

Asn Val Arg Gly Gly Arg Asp Ala Val Ile Leu Thr Cys Ala Ile
865               870                 875                 880

His Pro Glu Leu Ile Phe Thr Ile Thr Lys Ile Leu Leu Ala Ile Leu
              885                 890                 895

Gly Pro Leu Met Val Leu Gln Ala Gly Ile Thr Lys Val Pro Tyr Phe
              900                 905                 910

Val Arg Ala His Gly Leu Ile Arg Ala Cys Met Leu Val Arg Lys Val
              915                 920                 925

Ala Gly Gly His Tyr Val Gln Met Ala Leu Met Lys Leu Ala Ala Leu
              930                 935                 940

Thr Gly Thr Tyr Val Tyr Asp His Leu Thr Pro Leu Arg Asp Trp Ala
945               950                 955                 960

His Ala Gly Leu Arg Asp Leu Ala Val Ala Val Glu Pro Val Val Phe
              965                 970                 975

Ser Asp Met Glu Thr Lys Val Ile Thr Trp Gly Ala Asp Thr Ala Ala
              980                 985                 990

Cys Gly Asp Ile Ile Leu Gly Leu Pro Val Ser Ala Arg Arg Gly Arg
              995                 1000                1005

Glu Ile His Leu Gly Pro Ala Asp Ser Leu Glu Gly Gln Gly Trp Arg
              1010                1015                1020

Leu Leu Ala Pro Ile Thr Ala Tyr Ser Gln Gln Thr Arg Gly Leu Leu
1025              1030                1035                1040

Gly Cys Ile Ile Thr Ser Leu Thr Gly Arg Asp Arg Asn Gln Val Glu
              1045                1050                1055

Gly Glu Val Gln Val Val Ser Thr Ala Thr Gln Ser Phe Leu Ala Thr
              1060                1065                1070

Cys Val Asn Gly Val Cys Trp Thr Val Tyr His Gly Ala Gly Ser Lys
              1075                1080                1085

Thr Leu Ala Gly Pro Lys Gly Pro Ile Thr Gln Met Tyr Thr Asn Val
              1090                1095                1100

Asp Gln Asp Leu Val Gly Trp Gln Ala Pro Pro Gly Ala Arg Ser Leu
1105              1110                1115                1120

Thr Pro Cys Thr Cys Gly Ser Ser Asp Leu Tyr Leu Val Thr Arg His
              1125                1130                1135

Ala Asp Val Ile Pro Val Arg Arg Arg Gly Asp Ser Arg Gly Ser Leu

```
                1140                1145                1150
Leu Ser Pro Arg Pro Val Ser Tyr Leu Lys Gly Ser Gly Gly Pro
        1155                1160                1165

Leu Leu Cys Pro Ser Gly His Ala Val Gly Ile Phe Arg Ala Val
        1170                1175                1180

Cys Thr Arg Gly Val Ala Lys Ala Val Asp Phe Val Pro Val Glu Ser
1185                1190                1195                1200

Met Glu Thr Thr Met Arg Ser Pro Val Phe Thr Asp Asn Ser Ser Pro
                1205                1210                1215

Pro Ala Val Pro Gln Thr Phe Gln Val Ala His Leu His Ala Pro Thr
        1220                1225                1230

Gly Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly Phe
        1250                1255                1260

Gly Ala Tyr Met Ser Lys Ala His Gly Ile Asp Pro Asn Ile Arg Thr
1265                1270                1275                1280

Gly Val Arg Thr Ile Thr Thr Gly Ala Pro Ile Thr Tyr Ser Thr Tyr
                1285                1290                1295

Gly Lys Phe Leu Ala Asp Gly Gly Cys Ser Gly Gly Ala Tyr Asp Ile
        1300                1305                1310

Ile Ile Cys Asp Glu Cys His Ser Thr Asp Ser Thr Thr Ile Leu Gly
        1315                1320                1325

Ile Gly Thr Val Leu Asp Gln Ala Glu Thr Ala Gly Ala Arg Leu Val
        1330                1335                1340

Val Leu Ala Thr Ala Thr Pro Pro Gly Ser Val Thr Val Pro His Pro
1345                1350                1355                1360

Asn Ile Glu Glu Val Ala Leu Ser Ser Thr Gly Glu Ile Pro Phe Tyr
                1365                1370                1375

Gly Lys Ala Ile Pro Ile Glu Thr Ile Lys Gly Gly Arg His Leu Ile
        1380                1385                1390

Phe Cys His Ser Lys Lys Lys Cys Asp Glu Leu Ala Ala Lys Leu Ser
        1395                1400                1405

Gly Leu Gly Leu Asn Ala Val Ala Tyr Tyr Arg Gly Leu Asp Val Ser
        1410                1415                1420

Val Ile Pro Thr Ser Gly Asp Val Ile Val Val Ala Thr Asp Ala Leu
1425                1430                1435                1440

Met Thr Gly Phe Thr Gly Asp Phe Asp Ser Val Ile Asp Cys Asn Thr
                1445                1450                1455

Cys Val Thr Gln Thr Val Asp Phe Ser Leu Asp Pro Thr Phe Thr Ile
        1460                1465                1470

Glu Thr Thr Thr Val Pro Gln Asp Ala Val Ser Arg Ser Gln Arg Arg
        1475                1480                1485

Gly Arg Thr Gly Arg Gly Arg Met Gly Ile Tyr Arg Phe Val Thr Pro
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Ser
                1525                1530                1535

Val Arg Leu Arg Ala Tyr Leu Asn Thr Pro Gly Leu Pro Val Cys Gln
        1540                1545                1550

Asp His Leu Glu Phe Trp Glu Ser Val Phe Thr Gly Leu Thr His Ile
        1555                1560                1565
```

```
Asp Ala His Phe Leu Ser Gln Thr Lys Gln Ala Gly Asp Asn Phe Pro
    1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
        1620                1625                1630

Asn Glu Val Thr Thr Thr His Pro Ile Thr Lys Tyr Ile Met Ala Cys
            1635                1640                1645

Met Ser Ala Asp Leu Glu Val Val Thr Ser Thr Trp Val Leu Val Gly
    1650                1655                1660

Gly Val Leu Ala Ala Leu Ala Ala Tyr Cys Leu Thr Thr Gly Ser Val
1665                1670                1675                1680

Val Ile Val Gly Arg Ile Ile Leu Ser Gly Lys Pro Ala Ile Ile Pro
            1685                1690                1695

Asp Arg Glu Val Leu Tyr Arg Glu Phe Asp Glu Met Glu Glu Cys Ala
        1700                1705                1710

Ser His Leu Pro Tyr Ile Glu Gln Gly Met Gln Leu Ala Glu Gln Phe
            1715                1720                1725

Lys Gln Lys Ala Ile Gly Leu Leu Gln Thr Ala Thr Lys Gln Ala Glu
        1730                1735                1740

Ala Ala Ala Pro Val Val Glu Ser Lys Trp Arg Thr Leu Glu Ala Phe
1745                1750                1755                1760

Trp Ala Lys His Met Trp Asn Phe Ile Ser Gly Ile Gln Tyr Leu Ala
            1765                1770                1775

Gly Leu Ser Thr Leu Pro Gly Asn Pro Ala Ile Ala Ser Leu Met Ala
        1780                1785                1790

Phe Thr Ala Ser Ile Thr Ser Pro Leu Thr Thr Gln His Thr Leu Leu
            1795                1800                1805

Phe Asn Ile Leu Gly Gly Trp Val Ala Ala Gln Leu Ala Pro Pro Ser
        1810                1815                1820

Ala Ala Ser Ala Phe Val Gly Ala Gly Ile Ala Gly Ala Ala Val Gly
1825                1830                1835                1840

Ser Ile Gly Leu Gly Lys Val Leu Val Asp Ile Leu Ala Gly Tyr Gly
            1845                1850                1855

Ala Gly Val Ala Gly Ala Leu Val Ala Phe Lys Val Met Ser Gly Glu
        1860                1865                1870

Met Pro Ser Thr Glu Asp Leu Val Asn Leu Leu Pro Ala Ile Leu Ser
    1875                1880                1885

Pro Gly Ala Leu Val Val Gly Val Val Cys Ala Ala Ile Leu Arg Arg
    1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
            1925                1930                1935

Glu Ser Asp Ala Ala Ala Arg Val Thr Gln Ile Leu Ser Ser Leu Thr
        1940                1945                1950

Ile Thr Gln Leu Leu Lys Arg Leu His Gln Trp Ile Asn Glu Asp Cys
        1955                1960                1965

Ser Thr Pro Cys Ser Gly Ser Trp Leu Arg Asp Val Trp Asp Trp Ile
    1970                1975                1980

Cys Thr Val Leu Thr Asp Phe Lys Thr Trp Leu Gln Ser Lys Leu Leu
1985                1990                1995                2000
```

-continued

Pro Arg Leu Pro Gly Val Pro Phe Phe Ser Cys Gln Arg Gly Tyr Lys
            2005                2010                2015

Gly Val Trp Arg Gly Asp Gly Ile Met Gln Thr Thr Cys Pro Cys Gly
            2020                2025                2030

Ala Gln Ile Thr Gly His Val Lys Asn Gly Ser Met Arg Ile Val Gly
            2035                2040                2045

Pro Arg Thr Cys Ser Asn Thr Trp His Gly Thr Phe Pro Ile Asn Ala
            2050                2055                2060

Tyr Thr Thr Gly Pro Cys Thr Pro Ser Pro Ala Pro Asn Tyr Ser Arg
2065                2070                2075                2080

Ala Leu Trp Arg Val Ala Ala Glu Glu Tyr Val Glu Val Thr Arg Val
            2085                2090                2095

Gly Asp Phe His Tyr Val Thr Gly Met Thr Thr Asp Asn Val Lys Cys
            2100                2105                2110

Pro Cys Gln Val Pro Ala Pro Glu Phe Phe Thr Glu Val Asp Gly Val
            2115                2120                2125

Arg Leu His Arg Tyr Ala Pro Ala Cys Lys Pro Leu Leu Arg Glu Glu
            2130                2135                2140

Val Thr Phe Leu Val Gly Leu Asn Gln Tyr Leu Val Gly Ser Gln Leu
2145                2150                2155                2160

Pro Cys Glu Pro Glu Pro Asp Val Ala Val Leu Thr Ser Met Leu Thr
            2165                2170                2175

Asp Pro Ser His Ile Thr Ala Glu Thr Ala Lys Arg Arg Leu Ala Arg
            2180                2185                2190

Gly Ser Pro Pro Ser Leu Ala Ser Ser Ser Ala Ser Gln Leu Ser Ala
            2195                2200                2205

Pro Ser Leu Lys Ala Thr Cys Thr Thr Arg His Asp Ser Pro Asp Ala
            2210                2215                2220

Asp Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
            2245                2250                2255

Glu Pro Leu Gln Ala Glu Glu Asp Glu Arg Glu Val Ser Val Pro Ala
            2260                2265                2270

Glu Ile Leu Arg Arg Ser Arg Lys Phe Pro Arg Ala Met Pro Ile Trp
            2275                2280                2285

Ala Arg Pro Asp Tyr Asn Pro Pro Leu Leu Glu Ser Trp Lys Asp Pro
            2290                2295                2300

Asp Tyr Val Pro Pro Val Val His Gly Cys Pro Leu Pro Pro Ala Lys
2305                2310                2315                2320

Ala Pro Pro Ile Pro Pro Arg Arg Lys Arg Thr Val Val Leu Ser
            2325                2330                2335

Glu Ser Thr Val Ser Ser Ala Leu Ala Glu Leu Ala Thr Lys Thr Phe
            2340                2345                2350

Gly Ser Ser Glu Ser Ser Ala Val Asp Ser Gly Thr Ala Thr Ala Ser
            2355                2360                2365

Pro Asp Gln Pro Ser Asp Asp Gly Asp Ala Gly Ser Asp Val Glu Ser
            2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Glu Glu Ala Ser Glu Asp Val
            2405                2410                2415

Val Cys Cys Ser Met Ser Tyr Thr Trp Thr Gly Ala Leu Ile Thr Pro

```
                    2420            2425            2430
Cys Ala Ala Glu Glu Thr Lys Leu Pro Ile Asn Ala Leu Ser Asn Ser
        2435            2440            2445
Leu Leu Arg His His Asn Leu Val Tyr Ala Thr Thr Ser Arg Ser Ala
        2450            2455            2460
Ser Leu Arg Gln Lys Lys Val Thr Phe Asp Arg Leu Gln Val Leu Asp
2465            2470            2475            2480
Asp His Tyr Arg Asp Val Leu Lys Glu Met Lys Ala Lys Ala Ser Thr
            2485            2490            2495
Val Lys Ala Lys Leu Leu Ser Val Glu Glu Ala Cys Lys Leu Thr Pro
        2500            2505            2510
Pro His Ser Ala Arg Ser Lys Phe Gly Tyr Gly Ala Lys Asp Val Arg
        2515            2520            2525
Asn Leu Ser Ser Lys Ala Val Asn His Ile Arg Ser Val Trp Lys Asp
        2530            2535            2540
Leu Leu Glu Asp Thr Glu Thr Pro Ile Asp Thr Thr Ile Met Ala Lys
2545            2550            2555            2560
Asn Glu Val Phe Cys Val Gln Pro Glu Lys Gly Gly Arg Lys Pro Ala
            2565            2570            2575
Arg Leu Ile Val Phe Pro Asp Leu Gly Val Arg Val Cys Glu Lys Met
        2580            2585            2590
Ala Leu Tyr Asp Val Val Ser Thr Leu Pro Gln Ala Val Met Gly Ser
        2595            2600            2605
Ser Tyr Gly Phe Gln Tyr Ser Pro Gly Gln Arg Val Glu Phe Leu Val
        2610            2615            2620
Asn Ala Trp Lys Ala Lys Lys Cys Pro Met Gly Phe Ala Tyr Asp Thr
2625            2630            2635            2640
Arg Cys Phe Asp Ser Thr Val Thr Glu Asn Asp Ile Arg Val Glu Glu
            2645            2650            2655
Ser Ile Tyr Gln Cys Cys Asp Leu Ala Pro Glu Ala Arg Gln Ala Ile
        2660            2665            2670
Arg Ser Leu Thr Glu Arg Leu Tyr Ile Gly Gly Pro Leu Thr Asn Ser
        2675            2680            2685
Lys Gly Gln Asn Cys Gly Tyr Arg Arg Cys Arg Ala Ser Gly Val Leu
        2690            2695            2700
Thr Thr Ser Cys Gly Asn Thr Leu Thr Cys Tyr Leu Lys Ala Ala Ala
2705            2710            2715            2720
Ala Cys Arg Ala Ala Lys Leu Gln Asp Cys Thr Met Leu Val Cys Gly
            2725            2730            2735
Asp Asp Leu Val Val Ile Cys Glu Ser Ala Gly Thr Gln Glu Asp Glu
        2740            2745            2750
Ala Ser Leu Arg Ala Phe Thr Glu Ala Met Thr Arg Tyr Ser Ala Pro
        2755            2760            2765
Pro Gly Asp Pro Pro Lys Pro Glu Tyr Asp Leu Glu Leu Ile Thr Ser
        2770            2775            2780
Cys Ser Ser Asn Val Ser Val Ala His Asp Ala Ser Gly Lys Arg Val
2785            2790            2795            2800
Tyr Tyr Leu Thr Arg Asp Pro Thr Thr Pro Leu Ala Arg Ala Ala Trp
            2805            2810            2815
Glu Thr Ala Arg His Thr Pro Val Asn Ser Trp Leu Gly Asn Ile Ile
            2820            2825            2830
Met Tyr Ala Pro Thr Leu Trp Ala Arg Met Ile Leu Met Thr His Phe
        2835            2840            2845
```

```
Phe Ser Ile Leu Leu Ala Gln Glu Gln Leu Glu Lys Ala Leu Asp Cys
    2850                2855                2860
Gln Ile Tyr Gly Ala Cys Tyr Ser Ile Glu Pro Leu Asp Leu Pro Gln
2865                2870                2875                2880
Ile Ile Gln Arg Leu His Gly Leu Ser Ala Phe Ser Leu His Ser Tyr
            2885                2890                2895
Ser Pro Gly Glu Ile Asn Arg Val Ala Ser Cys Leu Arg Lys Leu Gly
        2900                2905                2910
Val Pro Pro Leu Arg Val Trp Arg His Arg Ala Arg Ser Val Arg Ala
    2915                2920                2925
Arg Leu Leu Ser Gln Gly Gly Arg Ala Ala Thr Cys Gly Lys Tyr Leu
    2930                2935                2940
Phe Asn Trp Ala Val Arg Thr Lys Leu Lys Leu Thr Pro Ile Pro Ala
2945                2950                2955                2960
Ala Ser Gln Leu Asp Leu Ser Ser Trp Phe Val Ala Gly Tyr Ser Gly
            2965                2970                2975
Gly Asp Ile Tyr His Ser Leu Ser Arg Ala Arg Pro Arg Trp Phe Met
        2980                2985                2990
Trp Cys Leu Leu Leu Leu Ser Val Gly Val Gly Ile Tyr Leu Leu Pro
    2995                3000                3005
Asn Arg
    3010

<210> SEQ ID NO 2
<211> LENGTH: 9605
<212> TYPE: DNA
<213> ORGANISM: Con 1 HCV isolate amino acid

<400> SEQUENCE: 2
gccagccccc gattgggggc gacactccac catagatcac tcccctgtga ggaactactg      60
tcttcacgca gaaagcgtct agccatggcg ttagtatgag tgtcgtgcag cctccaggac     120
cccccctccc gggagagcca tagtggtctg cggaaccggt gagtacaccg gaattgccag     180
gacgaccggg tcctttcttg gatcaacccg ctcaatgcct ggagatttgg gcgtgccccc     240
gcgagactgc tagccgagta gtgttgggtc gcgaaaggcc ttgtggtact gcctgatagg     300
gtgcttgcga gtgccccggg aggtctcgta gaccgtgcac catgagcacg aatcctaaac     360
ctcaaagaaa aaccaaacgt aacaccaacc gccgcccaca ggacgtcaag ttcccgggcg     420
gtggtcagat cgtcggtgga gtttacctgt tgccgcgcag gggccccagg ttgggtgtgc     480
gcgcgactag gaagacttcc gagcggtcgc aacctcgtgg aaggcgacaa cctatcccca     540
aggctcgcca gcccgagggt agggcctggg ctcagcccgg gtaccctggc cctctatg      600 gcaatgaggg cttgggtgg caggatggc tcctgtcacc ccgtggctct cggcctagtt      660 ggggcccac ggaccccgg cgtaggtcgc gcaatttggg taaggtcatc gatacctca       720 cgtgcggctt cgccgatctc atgggtaca ttccgctcgt cggcgccccc ctaggggcg       780 ctgccagggc cctggcgcat ggcgtccggg ttctggagga cggcgtgaac tatgcaacag     840
ggaatctgcc cggttgctcc ttttctatct tccttttggc tttgctgtcc tgtttgacca     900
tcccagcttc gcttatgaa gtgcgcaacg tatccggagt gtaccatgtc acgaacgact     960
gctccaacgc aagcattgtg tatgaggcag cggacatgat catgcatacc cccgggtgcg    1020
tgccctgcgt tcgggagaac aactcctccc gctgctgggt agcgctcact cccacgctcg    1080
cggccaggaa cgctagcgtc cccactacga cgatacgacg ccatgtcgat ttgctcgttg    1140
gggcggctgc tctctgctcc gctatgtacg tgggagatct ctgcggatct gttttcctcg    1200
```

```
tcgcccagct gttcaccttc tcgcctcgcc ggcacgagac agtacaggac tgcaattgct   1260
caatatatcc cggccacgtg acaggtcacc gtatggcttg ggatatgatg atgaactggt   1320
cacctacagc agccctagtg gtatcgcagt tactccggat cccacaagct gtcgtggata   1380
tggtggcggg ggcccattgg ggagtcctag cgggccttgc ctactattcc atggtgggga   1440
actgggctaa ggttctgatt gtgatgctac tctttgccgg cgttgacggg ggaacctatg   1500
tgacaggggg gacgatggcc aaaaacaccc tcgggattac gtccctcttt tcacccgggt   1560
catcccagaa aatccagctt gtaaacacca acggcagctg gcacatcaac aggactgccc   1620
tgaactgcaa tgactccctc aacactgggt tccttgctgc gctgttctac gtgcacaagt   1680
tcaactcatc tggatgccca gagcgcatgg ccagctgcag ccccatcgac gcgttcgctc   1740
aggggtgggg gcccatcact tacaatgagt cacacagctc ggaccagagg ccttattgtt   1800
ggcactacgc accccggccg tgcggtatcg tacccgcggc gcaggtgtgt ggtccagtgt   1860
actgcttcac cccaagccct gtcgtggtgg ggacgaccga ccggttcggc gtccctacgt   1920
acagttgggg ggagaatgag acggacgtgc tgcttcttaa caacacgcgg ccgccgcaag   1980
gcaactggtt tggctgtaca tggatgaata gcactgggtt caccaagacg tgcggggggcc   2040 ccccgtgtaa catcgggggg atcggcaata aaaccttgac ctgccccacg gactgcttcc   2100
ggaagcaccc cgaggccact tacaccaagt gtggttcggg gccttggttg acacccagat   2160
gcttggtcca ctaccatac aggctttggc actaccctg cactgtcaac tttaccatct   2220
tcaaggttag gatgtacgtg gggggagtgg agcacaggct cgaagccgca tgcaattgga   2280
ctcgaggaga gcgttgtaac ctggaggaca gggacagatc agagcttagc ccgctgctgc   2340
tgtctacaac ggagtggcag gtattgccct gttccttcac cacctaccg gctctgtcca   2400 ctggtttgat ccatctccat cagaacgtcg tggacgtaca atacctgtac ggtataggt   2460 cggcggttgt ctccttttgca atcaaatggg agtatgtcct gttgctcttc cttcttctgg   2520
cggacgcgcg cgtctgtgcc tgcttgtgga tgatgctgct gatagctcaa gctgaggccg   2580
ccctagagaa cctggtggtc ctcaacgcgg catccgtggc cggggcgcat ggcattctct   2640
ccttcctcgt gttcttctgt gctgcctggt acatcaaggg caggctggtc cctggggcgg   2700
catatgccct ctacgcgta tggccgctac tcctgctcct gctggcgtta ccaccacgag   2760
catacgccat ggaccgggag atggcagcat cgtgcggagg cgcggttttc gtaggtctga   2820
tactcttgac cttgtcaccg cactataagc tgttcctcgc taggctcata tggtggttac   2880 aatatttat caccagggcc gaggcacact tgcaagtgtg gatccccccc ctcaacgttc   2940 ggggggccg cgatgccgtc atcctcctca cgtgcgcgat ccaccagag ctaatcttta   3000 ccatcaccaa aatcttgctc gccatactcg gtccactcat ggtgctccag ctggtataa   3060 ccaaagtgcc gtacttcgtg cgcgcacacg ggctcattcg tgcatgcatg ctggtgcgga   3120
aggttgctgg gggtcattat gtccaaatgg ctctcatgaa gttggccgca ctgacaggta   3180
cgtacgttta tgaccatctc acccactgc gggactgggc ccacgcgggc ctacgagacc   3240
ttgcggtggc agttgagccc gtcgtcttct ctgatatgga gaccaaggtt atcacctggg   3300
gggcagacac cgcggcgtgt gggacatca tcttgggcct gccgtctcc gcccgcaggg   3360 ggagggagat acatctggga ccggcagaca gccttgaagg gcaggggtgg cgactcctcg   3420
cgcctattac ggcctactcc caacagacgc gaggcctact tggctgcatc atcactagcc   3480
tcacaggccg ggacaggaac caggtcgagg gggaggtcca agtggtctcc accgcaacac   3540 aatcttttcct ggcgacctgc gtcaatggcg tgtgttggac tgtctatcat ggtgccggct   3600
```

```
caaagaccct tgccggccca aagggcccaa tcacccaaat gtacaccaat gtggaccagg    3660
acctcgtcgg ctggcaagcg ccccccgggg cgcgttcctt gacaccatgc acctgcggca    3720
gctcggacct ttacttggtc acgaggcatg ccgatgtcat tccggtgcgc cggcggggcg    3780
acagcagggg gagcctactc tcccccaggc ccgtctccta cttgaagggc tcttcgggcg    3840
gtccactgct ctgcccctcg ggcacgctgt gggcatctt tcgggctgcc gtgtgcaccc     3900 gagggggttgc gaaggcggtg gactttgtac ccgtcgagtc tatggaaacc actatgcggt    3960
ccccggtctt cacggacaac tcgtcccctc cggccgtacc gcagacattc caggtggccc    4020
atctacacgc ccctactggt agcggcaaga gcactaaggt gccggctgcg tatgcagccc    4080
aagggtataa ggtgcttgtc ctgaacccgt ccgtcgccgc caccctaggt ttcgggggcgt    4140 atatgtctaa ggcacatggt atcgaccta acatcagaac cggggtaagg accatcacca     4200
cgggtgcccc catcacgtac tccacctatg caagtttct tgccgacggt ggttgctctg      4260
ggggcgccta tgacatcata atatgtgatg agtgccactc aactgactcg accactatcc    4320
tgggcatcgg cacagtcctg gaccaagcgg agacggctgg agcgcgactc gtcgtgctcg    4380
ccaccgctac gcctccggga tcggtcaccg tgccacatcc aaacatcgag gaggtggctc    4440
tgtccagcac tggagaaatc cccttttatg gcaaagccat ccccatcgag accatcaagg    4500 ggggaggca cctcattttc tgccattcca gaagaaatg tgatgagctc gccgcgaagc       4560
tgtccggcct cggactcaat gctgtagcat attaccgggg ccttgatgta ccgtcatac      4620 caactagcgg agacgtcatt gtcgtagcaa cggacgctct aatgacgggc tttaccggcg    4680
atttcgactc agtgatcgac tgcaatacat gtgtcaccca gacagtcgac ttcagcctgg    4740
acccgacctt caccattgag acgacgaccg tgccacaaga cgcggtgtca cgctcgcagc    4800
ggcgaggcag gactggtagg ggcaggatgg gcatttacag gtttgtgact ccaggagaac    4860
ggccctcggg catgttcgat tcctcggttc tgtgcgagtg ctatgacgcg ggctgtgctt    4920
ggtacgagct cacgcccgcc gagacctcag ttaggttgcg ggcttaccta aacacaccag    4980
ggttgcccgt ctgccaggac catctggagt tctgggagag cgtctttaca ggcctcaccc    5040
acatagacgc ccatttcttg tcccagacta agcaggcagg agacaacttc ccctacctgg    5100
tagcatacca ggctacggtg tgcgccaggg ctcaggctcc acctccatcg tgggaccaaa    5160
tgtggaagtg tctcatacgg ctaaagccta cgctgcacgg gccaacgccc tgctgtata     5220 ggctgggagc cgttcaaaac gaggttacta ccacacaccc cataaccaaa tacatcatgg    5280
catgcatgtc ggctgacctg gaggtcgtca cgagcacctg ggtgctggta ggcggagtcc    5340
tagcagctct ggccgcgtat tgcctgacaa caggcagcgt ggtcattgtg gcaggatca    5400 tcttgtccgg aaagccggcc atcattcccg acagggaagt cctttaccgg gagttcgatg    5460
agatggaaga gtgcgcctca cacctcccctt acatcgaaca gggaatgcag ctcgccgaac    5520
aattcaaaca gaaggcaatc gggttgctgc aaacagccac caagcaagcg gaggctgctg    5580
ctcccgtggt ggaatccaag tggcggaccc tcgaagcctt ctgggcgaag catatgtgga    5640
atttcatcag cgggatacaa tatttagcag gcttgtccac tctgcctggc aacccgcgca    5700
tagcatcact gatggcattc acagcctcta tcaccagccc gctcaccacc caacataccc    5760 tcctgttaa catcctgggg ggatgggtgg ccgcccaact tgctcctccc agcgctgctt     5820 ctgcttttcgt aggcgccggc atcgctggag cggctgttgg cagcataggc cttgggaagg    5880
tgcttgtgga tattttggca ggttatggag caggggtggc aggcgcgctc gtggcccttta    5940 aggtcatgag cggcgagatg ccctccaccg aggacctggt taacctactc cctgctatcc    6000
```

```
tctcccctgg cgccctagtc gtcgggtcg tgtgcgcagc gatactgcgt cggcacgtgg    6060
gcccagggga gggggctgtg cagtggatga accggctgat agcgttcgct tcgcggggta    6120
accacgtctc ccccacgcac tatgtgcctg agagcgacgc tgcagcacgt gtcactcaga    6180
tcctctctag tcttaccatc actcagctgc tgaagaggct tcaccagtgg atcaacgagg    6240
actgctccac gccatgctcc ggctcgtggc taagagatgt ttgggattgg atatgcacgg    6300
tgttgactga tttcaagacc tggctccagt ccaagctcct gccgcgattg ccgggagtcc    6360
ccttcttctc atgtcaacgt gggtacaagg gagtctggcg gggcgacggc atcatgcaaa    6420
ccacctgccc atgtggagca cagatcaccg acatgtgaa aaacggttcc atgaggatcg    6480
tggggcctag gacctgtagt aacacgtggc atggaacatt ccccattaac gcgtacacca    6540
cgggcccctg cacgccctcc ccggcgccaa attattctag ggcgctgtgg cgggtggctg    6600
ctgaggagta cgtggaggtt acgcgggtgg gggatttcca ctacgtgacg gcatgaccaa    6660
ctgacaacgt aaagtgcccg tgtcaggttc cggcccccga attcttcaca gaagtggatg    6720
gggtgcggtt gcacaggtac gctccagcgt gcaaacccct cctacgggag gaggtcacat    6780
tcctggtcgg gctcaatcaa tacctggttg ggtcacagct cccatgcgag cccgaaccgg    6840
acgtagcagt gctcacttcc atgctcaccg accctccca cattacggcg gagacggcta    6900
agcgtaggct ggcaggggga tctccccccct ccttggccag ctcatcagct agccagctgt    6960
ctgcgccttc cttgaaggca acatgcacta cccgtcatga ctccccggac gctgacctca    7020
tcgaggccaa cctcctgtgg cggcaggaga tgggcgggaa catcacccgc gtggagtcag    7080
aaaataaggt agtaattttg gactctttcg agccgctcca agcggaggag gatgagaggg    7140
aagtatccgt tccggcggag atcctgcgga ggtccaggaa attccctcga gcgatgccca    7200
tatgggcacg cccggattac aaccctccac tgttagagtc ctggaaggac ccggactacg    7260 tccctcagt ggtacacggg tgtccattgc cgcctgccaa ggcccctccg ataccacctc    7320
cacggaggaa gaggacggtt gtcctgtcag aatctaccgt gtcttctgcc ttggcggagc    7380
tcgccacaaa gaccttcggc agctccgaat cgtcggccgt cgacagcggc acggcaacgg    7440
cctctcctga ccagccctcc gacgacggcg acgcgggatc cgacgttgag tcgtactcct    7500
ccatgccccc ccttgagggg gagccggggg atcccgatct cagcgacggg tcttggtcta    7560
ccgtaagcga ggaggctagt gaggacgtcg tctgctgctc gatgtcctac acatggacag    7620
gcgccctgat cacgccatgc gctgcggagg aaaccaagct gcccatcaat gcactgagca    7680
actctttgct ccgtcaccac aacttggtct atgctacaac atctcgcagc gcaagcctgc    7740
ggcagaagaa ggtcaccttt gacagactgc aggtcctgga cgaccactac cgggacgtgc    7800
tcaaggagat gaaggcgaag gcgtccacag ttaaggctaa acttctatcc gtggaggaag    7860
cctgtaagct gacgccccca cattcggcca gatctaaatt tggctatggg gcaaggacg    7920 tccggaacct atccagcaag gccgttaacc acatccgctc cgtgtggaag gacttgctgg    7980
aagacactga gacaccaatt gacaccacca tcatggcaaa aaatgaggtt ttctgcgtcc    8040
aaccagagaa ggggggccgc aagccagctc gccttatcgt attcccagat ttgggggttc    8100
gtgtgtgcga gaaaatggcc ctttacgatg tggtctccac cctccctcag gccgtgatgg    8160
gctcttcata cggattccaa tactctcctg gacagcgggc cgagttcctg gtgaatgcct    8220
ggaaagcgaa gaaatgccct atgggcttcg catatgacac ccgctgtttt gactcaacgg    8280
tcactgagaa tgacatccgt gttgaggagt caatctacca atgttgtgac ttggccccccg    8340 aagccagaca ggccataagg tcgctcacag agcggcttta tcatcggggc cccctgacta    8400
```

```
attctaaagg gcagaactgc ggctatcgcc ggtgccgcgc gagcggtgta ctgacgacca      8460
gctgcggtaa taccctcaca tgttacttga aggccgctgc ggcctgtcga gctgcgaagc      8520
tccaggactg cacgatgctc gtatgcggag acgaccttgt cgttatctgt gaaagcgcgg      8580
ggacccaaga ggacgaggcg agcctacggg ccttcacgga ggctatgact agatactctg      8640
ccccccctgg ggaccccgccc aaaccagaat acgacttgga gttgataaca tcatgctcct      8700
ccaatgtgtc agtcgcgcac gatgcatctg gcaaagggg gtactatctc acccgtgacc      8760
ccaccacccc ccttgcgcgg gctgcgtggg agacagctag acacactcca gtcaattcct      8820
ggctaggcaa catcatcatg tatgcgccca ccttgtgggc aaggatgatc ctgatgactc      8880
atttcttctc catccttcta gctcaggaac aacttgaaaa agccctagat tgtcagatct      8940
acggggcctg ttactccatt gagccacttg acctacctca gatcattcaa cgactccatg      9000
gccttagcgc attttcactc catagttact ctccaggtga gatcaatagg gtggcttcat      9060
gcctcaggaa acttggggta ccgcccttgc gagtctggga catcgggcc agaagtgtcc       9120 gcgctaggct actgtcccag ggggggaggg ctgccacttg tggcaagtac ctcttcaact      9180
gggcagtaag gaccaagctc aaactcactc caatcccggc tgcgtcccag ttggatttat      9240
ccagctggtt cgttgctggt tacagcgggg gagacatata tcacagcctg tctcgtgccc      9300
gaccccgctg gttcatgtgg tgcctactcc tactttctgt aggggtaggc atctatctac      9360
tccccaaccg atgaacgggg agctaaacac tccaggccaa taggccatcc tgttttttc      9420 ccttttttt tttctttttt tttttttttt tttttttttct cctttttttt      9480 tcctcttttt ttccttttct ttcctttggt ggctccatct tagccctagt cacggctagc      9540
tgtgaaaggt ccgtgagccg cttgactgca gagagtgctg atactggcct ctctgcagat      9600
caagt                                                                  9605

<210> SEQ ID NO 3
<211> LENGTH: 10690
<212> TYPE: DNA
<213> ORGANISM: pHCVNeo.17 coding

<400> SEQUENCE: 3
gccagccccc gattggggc gacactccac catagatcac tcccctgtga ggaactactg        60
tcttcacgca gaaagcgtct agccatggcg ttagtatgag tgtcgtgcag cctccaggac      120 ccccctccc gggagagcca tagtggtctg cggaaccggt gagtacaccg gaattgccag      180
gacgaccggg tcctttcttg gatcaacccg ctcaatgcct ggagatttgg gcgtgccccc      240
gcgagactgc tagccgagta gtgttgggtc gcgaaaggcc ttgtggtact gcctgatagg      300
gtgcttgcga gtgccccggg aggtctcgta gaccgtgcac catgagcacg aatcctaaac      360
ctcaaagaaa aaccaaaggg cgcgccatga ttgaacaaga tggattgcac gcaggttctc      420
cggccgcttg ggtggagagg ctattcggct atgactgggc acaacagaca atcggctgct      480
ctgatgccgc cgtgttccgg ctgtcagcgc aggggcgccc ggttcttttt gtcaagaccg      540
acctgtccgg tgccctgaat gaactgcagg acgaggcagc gcggctatcg tggctggcca      600
cgacgggcgt tccttgcgca gctgtgctcg acgttgtcac tgaagcggga agggactggc      660
tgctattggg cgaagtgccg gggcaggatc tcctgtcatc tcaccttgct cctgccgaga      720
aagtatccat catggctgat gcaatgcggc ggctgcatac gcttgatccg gctacctgcc      780
cattcgacca ccaagcgaaa catcgcatcg agcgagcacg tactcggatg gaagccggtc      840
ttgtcgatca ggatgatctg gacgaagagc atcaggggct cgcgccagcc gaactgttcg      900
```

```
ccaggctcaa ggcgcgcatg cccgacggcg aggatctcgt cgtgacccat ggcgatgcct    960
gcttgccgaa tatcatggtg gaaaatggcc gcttttctgg attcatcgac tgtggccggc   1020
tgggtgtggc ggaccgctat caggacatag cgttggctac ccgtgatatt gctgaagagc   1080
ttggcggcga atgggctgac cgcttcctcg tgctttacgg tatcgccgct cccgattcgc   1140
agcgcatcgc cttctatcgc cttcttgacg agttcttctg agtttaaaca gaccacaacg   1200
gtttccctct agcgggatca attccgcccc tctccctccc cccccctaa cgttactggc    1260
cgaagccgct tggaataagg ccggtgtgcg tttgtctata tgttattttc caccatattg   1320
ccgtcttttg gcaatgtgag ggcccggaaa cctggccctg tcttcttgac gagcattcct   1380
aggggtcttt cccctctcgc caaaggaatg caaggtctgt tgaatgtcgt gaaggaagca   1440
gttcctctgg aagcttcttg aagacaaaca acgtctgtag cgacccttg caggcagcgg    1500
aaccccccac ctggcgacag gtgcctctgc ggccaaaagc cacgtgtata agatacacct   1560
gcaaaggcgg cacaacccca gtgccacgtt gtgagttgga tagttgtgga aagagtcaaa   1620
tggctctcct caagcgtatt caacaagggg ctgaaggatg cccagaaggt accccattgt   1680
atgggatctg atctggggcc tcggtgcaca tgctttacat tgttagtc gaggttaaaa     1740
aacgtctagg ccccccgaac cacggggacg tggttttcct ttgaaaaaca cgataatacc   1800
atggcgccta ttacgcccta ctcccaacag acgcgaggcc tacttggctg catcatcact   1860
agcctcacag gccgggacag gaaccaggtc gaggggagg tccaagtggt ctccaccgca    1920
acacaatctt tcctggcgac ctgcgtcaat ggcgtgtgtt ggactgtcta tcatggtgcc   1980
ggctcaaaga cccttgccgg cccaaagggc ccaatcaccc aaatgtacac caatgtggac   2040
caggacctcg tcggctggca agcgcccccc ggggcgcgtt ccttgacacc atgcacctgc   2100
ggcagctcgg acctttactt ggtcacgagg catgccgatg tcattccggt gcgccggcgg   2160
ggcgacagca gggggagcct actctccccc aggcccgtct cctacttgaa gggctcttcg   2220
ggcggtccac tgctctgccc ctcggggcac gctgtgggca tctttcgggc tgccgtgtgc   2280
acccgagggg ttgcgaaggc ggtggacttt gtaccgtcg agtctatgga aaccactatg    2340
cggtccccgg tcttcacgga caactcgtcc cctccggccg taccgcagac attccaggtg   2400
gcccatctac acgcccctac tggtagcggc aagagcacta aggtgccggc tgcgtatgca   2460
gcccaagggt ataaggtgct tgtcctgaac ccgtccgtcg ccgccaccct aggtttcggg   2520
gcgtatatgt ctaaggcaca tggtatcgac cctaacatca gaaccggggt aaggaccatc   2580
accacgggtg cccccatcac gtactccacc tatggcaagt ttcttgccga cggtggttgc   2640
tctgggggcg cctatgacat cataatatgt gatgagtgcc actcaactga ctcgaccact   2700
atcctgggca tcggcacagt cctggaccaa gcggagacgg ctggagcgcg actcgtcgtg   2760
ctcgccaccg ctacgcctcc gggatcggtc accgtgccac atccaaacat cgaggaggtg   2820
gctctgtcca gcactggaga aatcccttt tatggcaaag ccatcccat cgagaccatc     2880
aagggggga ggcacctcat tttctgccat tccaagaaga atgtgatga gctcgccgcg     2940
aagctgtccg gcctcggact caatgctgta gcatattacc ggggccttga tgtatccgtc   3000
ataccaacta gcgagacgt cattgtcgta gcaacggacg ctctaatgac gggctttacc    3060
ggcgatttcg actcagtgat cgactgcaat acatgtgtca cccagacagt cgacttcagc   3120
ctggacccga ccttcaccat tgagacgacg accgtgccac aagacgcggt gtcacgctcg   3180
cagcggcgag gcaggactgg taggggcagg atgggcattt acaggtttgt gactccagga   3240
gaacggccct cgggcatgtt cgattcctcg gttctgtgcg agtgctatga cgcgggctgt   3300
```

```
gcttggtacg agctcacgcc cgccgagacc tcagttaggt tgcgggctta cctaaacaca    3360
ccagggttgc ccgtctgcca ggaccatctg gagttctggg agagcgtctt tacaggcctc    3420
acccacatag acgcccattt cttgtcccag actaagcagg caggagacaa cttccctac     3480
ctggtagcat accaggctac ggtgtgcgcc agggctcagg ctccacctcc atcgtgggac    3540
caaatgtgga agtgtctcat acggctaaag cctacgctgc acgggccaac gcccctgctg    3600
tataggctgg gagccgttca aaacgaggtt actaccacac accccataac caaatacatc    3660
atggcatgca tgtcggctga cctggaggtc gtcacgagca cctgggtgct ggtaggcgga    3720
gtcctagcag ctctggccgc gtattgcctg acaacaggca gcgtggtcat tgtgggcagg    3780
atcatcttgt ccggaaagcc ggccatcatt cccgacaggg aagtccttta ccgggagttc    3840
gatgagatgg aagagtgcgc ctcacacctc ccttacatcg aacagggaat gcagctcgcc    3900
gaacaattca aacagaaggc aatcgggttg ctgcaaacag ccaccaagca agcggaggct    3960
gctgctcccg tggtggaatc caagtggcgg accctcgaag ccttctgggc gaagcatatg    4020
tggaatttca tcagcgggat acaatattta gcaggcttgt ccactctgcc tggcaacccc    4080
gcgatagcat cactgatggc attcacagcc tctatcacca gcccgctcac cacccaacat    4140
accctcctgt ttaacatcct ggggggatgg gtggccgccc aacttgctcc tcccagcgct    4200
gcttctgctt tcgtaggcgc cggcatcgct ggagcggctg ttggcagcat aggccttggg    4260
aaggtgcttg tggatatttt ggcaggttat ggagcagggg tggcaggcgc gctcgtggcc    4320
tttaaggtca tgagcggcga gatgcctcc accgaggacc tggttaacct actccctgct    4380
atcctctccc ctggcgccct agtcgtcggg gtcgtgtgcg cagcgatact gcgtcggcac    4440
gtgggcccag gggaggggc tgtgcagtgg atgaaccggc tgatagcgtt cgcttcgcgg    4500
ggtaaccacg tctcccccac gcactatgtg cctgagagcg acgctgcagc acgtgtcact    4560
cagatcctct ctagtcttac catcactcag ctgctgaaga ggcttcacca gtggatcaac    4620
gaggactgct ccacgccatg ctccggctcg tggctaagag atgtttggga ttggatatgc    4680
acggtgttga ctgatttcaa gacctggctc cagtccaagc tcctgccgcg attgccggga    4740
gtccccttct tctcatgtca acgtgggtac aagggagtct ggcggggcga cggcatcatg    4800
caaaccacct gcccatgtgg agcacagatc accggacatg tgaaaaacgg ttccatgagg    4860
atcgtggggc ctaggacctg tagtaacacg tggcatggaa cattccccat taacgcgtac    4920
accacgggcc cctgcacgcc ctcccgggcg ccaaattatt ctagggcgct gtggcgggtg    4980
gctgctgagg agtacgtgga ggttacgcgg gtgggggatt tccactacgt gacgggcatg    5040
accactgaca acgtaaagtg cccgtgtcag gttccggccc ccgaattctt cacagaagtg    5100
gatggggtgc ggttgcacag gtacgctcca gcgtgcaaac ccctcctacg ggaggaggtc    5160
acattcctgg tcgggctcaa tcaatacctg gttgggtcac agctcccatg cgagcccgaa    5220
ccggacgtag cagtgctcac ttccatgctc accgacccct cccacattac ggcggagacg    5280
gctaagcgta ggctggccag gggatctccc ccctccttgg ccagctcatc agctagccag    5340
ctgtctgcgc cttccttgaa ggcaacatgc actacccgtc atgactcccc ggacgctgac    5400
ctcatcgagg ccaacctcct gtggcggcag gagatggggc gaacatcac ccgcgtggag    5460
tcagaaaata aggtagtaat tttggactct ttcgagccgc tccaagcgga ggaggatgag    5520
agggaagtat ccgttccggc ggagatcctg cggaggtcca ggaaattccc tcgagcgatg    5580
cccatatggg cacgccgga ttacaaccct ccactgttag agtcctggaa ggaccccgac    5640
tacgtccctc cagtggtaca cgggtgtcca ttgccgcctg ccaaggcccc tccgatacca    5700
```

```
cctccacgga ggaagaggac ggttgtcctg tcagaatcta ccgtgtcttc tgccttggcg   5760
gagctcgcca caaagacctt cggcagctcc gaatcgtcgg ccgtcgacag cggcacggca   5820
acggcctctc ctgaccagcc ctccgacgac ggcgacgcgg gatccgacgt tgagtcgtac   5880
tcctccatgc ccccccttga gggggagccg ggggatcccg atctcagcga cgggtcttgg   5940
tctaccgtaa gcgaggaggc tagtgaggac gtcgtctgct gctcgatgtc ctacacatgg   6000
acaggcgccc tgatcacgcc atgcgctgcg gaggaaacca agctgcccat caatgcactg   6060
agcaactctt tgctccgtca ccacaacttg gtctatgcta caacatctcg cagcgcaagc   6120
ctgcggcaga agaaggtcac ctttgacaga ctgcaggtcc tggacgacca ctaccgggac   6180
gtgctcaagg agatgaaggc gaaggcgtcc acagttaagg ctaaacttct atccgtggag   6240
gaagcctgta agctgacgcc cccacattcg gccagatcta aatttggcta tggggcaaag   6300
gacgtccgga acctatccag caaggccgtt aaccacatcc gctccgtgtg aaggacttg    6360 ctggaagaca ctgagacacc aattgacacc accatcatgg caaaaaatga gttttctgc    6420 gtccaaccag agaagggggg ccgcaagcca gctcgcctta tcgtattccc agatttgggg   6480
gttcgtgtgt gcgagaaaat ggcccTTTac gatgtggtct ccaccctccc tcaggccgtg   6540
atgggctctt catacggatt ccaatactct cctggacagc gggtcgagtt cctggtgaat   6600
gcctggaaag cgaagaaatg ccctatgggc ttcgcatatg acaccgctg ttttgactca    6660 acggtcactg agaatgacat ccgtgttgag gagtcaatct accaatgttg tgacttggcc   6720
cccgaagcca gacaggccat aaggtcgctc acagagcggc tttacatcgg gggcccctg    6780 actaattcta aagggcagaa ctgcggctat cgccggtgcc gcgcgagcgg tgtactgacg   6840
accagctgcg gtaatacccT cacatgttac ttgaaggccg ctgcggcctg tcgagctgcg   6900
aagctccagg actgcacgat gctcgtatgc ggagacgacc ttgtcgttat ctgtgaaagc   6960
gcggggaccc aagaggacga ggcgagccta cgggccttca cggaggctat gactagatac   7020
tctgcccccc ctggggaccc gcccaaacca gaatacgact tggagttgat aacatcatgc   7080
tcctccaatg tgtcagtcgc gcacgatgca tctggcaaaa gggtgtacta tctcacccgt   7140
gaccccacca ccccccttgc gcgggctgcg tgggagacag ctagacacac tccagtcaat   7200
tcctggctag caacatcat catgtatgcg cccaccttgt gggcaaggat gatcctgatg    7260
actcattTct tctccatcct tctagctcag gaacaacttg aaaaagccct agattgtcag   7320
atctacgggg cctgttactc cattgagcca cttgacctac ctcagatcat tcaacgactc   7380
catggcctta gcgcatttTc actccatagt tactctccag gtgagatcaa tagggtggct   7440
tcatgcctca ggaaacttgg ggtaccgcc ttgcgagtct ggagacatcg ggccagaagt    7500
gtccgcgcta ggctactgtc caggggggg agggctgcca cttgtggcaa gtacctcttc    7560
aactgggcag taaggaccaa gctcaaactc actccaatcc cggctgcgtc ccagttggat   7620
ttatccagct ggttcgttgc tggttacagc gggggagaca tatatcacag cctgtctcgt   7680
gcccgacccc gctggttcat gtggtgccta ctcctacttt ctgtaggggt aggcatctat   7740
ctactcccca accgatgaac ggggagctaa acactccagg ccaataggcc atcctgtttt   7800
tttccctttt tttttttctt tttttttttt tttttttttt tttttttttt ttctcctttt   7860
tttttcctct tttttttcctt tctttccttt tggtggctcc atcttagccc tagtcacggc  7920
tagctgtgaa aggtccgtga ccgcttgac tgcagagagt gctgatactg gcctctctgc    7980
agatcaagta cttctagaga attctagctt ggcgtaatca tggtcatagc tgtttcctgt   8040
gtgaaattgt tatcagctca caattccaca caacatacga gccggaagca taaagtgtaa   8100
```

```
agcctgggat gcctaatgag tgagctaact cacattagtt gcgttgcgct cactgcccgc    8160
tttccagtcg ggaaacctgt cgtgccagct ccattagtga atcgtccaac gcacggggag    8220
aggcggtttg cgtattgggc gcacttccgc ttcctcgctc actgactcgc tgcgctcgtt    8280
cgttcggctg cggcgagccg tatcagctca ctcaaaggcg gtaatacggt tatccacaga    8340
atcaggggat aacgcaggaa agaccatgtg agcaaaaggc cagcaaaagg ccaggaaccg    8400
taaaaaggcc gcgttgctgg cgttttttcca taggctccgc cccccctgacg agcatcacaa    8460 aaatcgacgc tcaagtcaga ggtggcgaaa cccgacagga ctataaagat accaggcgtt    8520 tcccctgga agctccctcg tgcgctctcc tgttccgacc ctgccgctta ccggatacct    8580
gtccgccttt ctcccttcgg gaagcgtggc gctttctcat agctcacgct gtaggtatct    8640
cagttcggtg taggtcgttc gctccaagct gggctgtgtg cacgaacccc ccgttcagcc    8700
cgaccgctgc gccttatccg gtaactatcg tcttgagtcc aacccggtaa gacacgactt    8760
atcgccactg gcagcagcca ctggtaacag gattagcaga gcgaggtatg taggcggtgc    8820
tacagagttc ttgaagtggt ggcctaacta cggctacact agaaggacag tatttggtat    8880
ctgcgctctg ctgaagccag ttaccttcgg aaaaagagtt ggtagctctt gatccggcaa    8940
acaaaccacc gctggtagcg gtggtttttt tgtttgcaag cagcagatta cgcgcagaaa    9000
aaaaggatct caagaagatc ctttgatctt ttctacgggg tctgacgctc agtggaacga    9060
aaactcacgt taagggattt tggtcatgag attatcaaaa aggatcttca cctagatcct    9120
tttaaattaa aaatgaagtt ttaaatcaat ctaaagtata tatgagtaaa cttggtctga    9180
cagttaccaa tgcttaatca gtgaggcacc tatctcagcg atctgtctat ttcgttcatc    9240
catagttgcc tgactcccg tcgtgtagat aactacgata cgggagggct taccatctgg    9300
ccccagtgct gcaatgatac cgcgagaacc acgctcaccc gcaccagatt tatcagcaat    9360
aaaccagcca gccggaagtg cgctgcggag aagtggtcct gcaactttat ccgcctccat    9420
ccagtctatt agttgttgcc gggaagctag agtaagtagt tcgccagtca gcagtttgcg    9480
taacgtcgtt gccatagcaa caggcatcgt ggtgtcacgc tcgtcgtttg gtatggcttc    9540
attcagctcc ggctcccaac gatcaaggcg agttacatga tcccccatgt tgtgcaaaaa    9600
agcggttagc tccttcggtc ctccgatcgt tgtcagaagt aagttggccg cagtgttatc    9660
actcatggtt atggcagcac tgcataattc tcttactgtc atgccatccg taagatgctt    9720
ttctgtgact ggtgagtact caaccaagtc attctgagaa tagtgtatgc ggcgaccgag    9780
ttgctcttgc ccggcgtcaa tacgggataa taccgcgcca catagcagaa ctttaaaagt    9840
gctcatcatt ggaaaacgtt cttcggggcg aaaactctca aggatcttac cgctgttgag    9900
atccagttcg atgtaaccca ctcgtgcacc caactgatct tcagcatctt ttactttcac    9960
cagcgtttct gggtgagcaa aaacaggaag gcaaaatgcc gcaaaaaagg gaataagggc    10020
gacacggaaa tgttgaatac tcatactctt cctttttcaa tattattgaa gcatttatca    10080
gggttattgt ctcatgagcg gatacatatt tgaatgtatt tagaaaaata aacaaatagg    10140
ggttccgcgc acatttcccc gaaaagtgcc acctgacgtc taagaaacca ttattaccat    10200
gacattaacc tataaaaata ggcgtatcac gaagcccttt cgtctagcgc gtttcggtga    10260
tgacggtgaa aacctctgac acttgcagct cccgcagacg gtcacagctt gtctgtaagc    10320
ggatgccggg agcaggcaag cccgtcaggg cgcgtcagtg ggtgttggcg ggtgtcgggg    10380
ctggcttaac tatgcggcat cagagcagat tgtactgaga gtacaccaga tgcggtgtga    10440
aataccgcac agatgcgtaa ggagaaaata ccgcatcagc ctccattcgc cattcagact    10500
```

```
ccgcaactgt tgggaagggc ggtcagtacg cgcttcttcg ctattacgcc aactggcgaa    10560
agggggatgt gctgcaaggc gattaagttg ggtaacgcca gggttttccc aatcacgacg    10620
ttgtaaaacg acagccaatg aattgaagct tattaattct agactgaagc ttttaatacg    10680
actcactata                                                           10690

<210> SEQ ID NO 4
<211> LENGTH: 23
<212> TYPE: DNA
<213> ORGANISM: Primer oligonucleotide

<400> SEQUENCE: 4
acatgatctg cagagaggcc agt                                               23

<210> SEQ ID NO 5
<211> LENGTH: 26
<212> TYPE: DNA
<213> ORGANISM: Primer oligonucleotide

<400> SEQUENCE: 5
gacasgctgt gatawatgtc tccccc                                            26

<210> SEQ ID NO 6
<211> LENGTH: 21
<212> TYPE: DNA
<213> ORGANISM: Primer oligonucleotide

<400> SEQUENCE: 6
tggctctcct caagcgtatt c                                                 21

<210> SEQ ID NO 7
<211> LENGTH: 23
<212> TYPE: DNA
<213> ORGANISM: Primer oligonucleotide

<400> SEQUENCE: 7
actctctgca gtcaagcggc tca                                               23

<210> SEQ ID NO 8
<211> LENGTH: 21
<212> TYPE: DNA
<213> ORGANISM: Primer oligonucleotide

<400> SEQUENCE: 8
cagtggatga accggctgat a                                                 21

<210> SEQ ID NO 9
<211> LENGTH: 23
<212> TYPE: DNA
<213> ORGANISM: Primer oligonucleotide

<400> SEQUENCE: 9
ggggcgacgg catcatgcaa acc                                               23

<210> SEQ ID NO 10
<211> LENGTH: 23
<212> TYPE: DNA
<213> ORGANISM: Primer oligonucleotide

<400> SEQUENCE: 10
caggacctgc agtctgtcaa agg                                               23
```

```
<210> SEQ ID NO 11
<211> LENGTH: 17
<212> TYPE: DNA
<213> ORGANISM: Primer oligonucleotide

<400> SEQUENCE: 11
cgggagagcc atagtgg                                                  17

<210> SEQ ID NO 12
<211> LENGTH: 19
<212> TYPE: DNA
<213> ORGANISM: Primer oligonucleotide

<400> SEQUENCE: 12
agtaccacaa ggcctttcg                                                19

<210> SEQ ID NO 13
<211> LENGTH: 21
<212> TYPE: DNA
<213> ORGANISM: Probe

<400> SEQUENCE: 13
ctgcggaacc ggtgagtaca c                                             21
```

HEPATITIS C VIRUS REPLICONS AND REPLICON ENHANCED CELLS

CROSS-REFERENCE TO RELATED APPLICATIONS

The present application claims priority to U.S. Ser. No. 60/263,479, filed Jan. 23, 2001, hereby incorporated by reference herein.

BACKGROUND OF THE INVENTION

The references cited in the present application are not admitted to be prior art to the claimed invention.

It is estimated that about 3% of the world's population are infected with the Hepatitis C virus (HCV). (Wasley, et al. 2000. *Semin. Liver Dis.* 20, 1-16.) Exposure to HCV results in an overt acute disease in a small percentage of cases, while in most instances the virus establishes a chronic infection causing liver inflammation and slowly progresses into liver failure and cirrhosis. (Iwarson, 1994. *FEMS Microbiol. Rev.* 14, 201-204.) In addition, epidemiological surveys indicate an important role of HCV in the pathogenesis of hepatocellular carcinoma. (Kew, 1994. *FEMS Microbiol. Rev.* 14, 211-220, Alter, 1995. *Blood* 85, 1681-1695.)

The HCV genome consists of a single strand RNA of about 9.5 kb in length, encoding a precursor polyprotein of about 3000 amino acids. (Choo, et al., 1989. *Science* 244, 362-364, Choo, et al., 1989. *Science* 244, 359-362, Takamizawa, et al., 1991. *J. Virol.* 65, 1105-1113.) The HCV polyprotein contains the viral proteins in the order: C-E1-E2-p7-NS2-NS3-NS4A-NS4B-NS5A-NS5B.

Individual viral proteins are produced by proteolysis of the HCV polyprotein. Host cell proteases release the putative structural proteins C, E1, E2, and p7, and create the N-terminus of NS2 at amino acid 810. (Mizushima, et al., 1994. *J. Virol.* 68, 2731-2734, Hijikata, et al., 1993. *P.N.A.S. USA* 90, 10773-10777.)

The non-structural proteins NS3, NS4A, NS4B, NS5A and NS5B presumably form the virus replication machinery and are released from the polyprotein. A zinc-dependent protease associated with NS2 and the N-terminus of NS3 is responsible for cleavage between NS2 and NS3. (Grakoui, et al, 1993. *J. Virol.* 67, 1385-1395, Hijikata, et al., 1993. *P.N.A.S. USA* 90, 10773-10777.) A distinct serine protease located in the N-terminal domain of NS3 is responsible for proteolytic cleavages at the NS3/NS4A, NS4A/NS4B, NS4B/NS5A and NS5A/NS5B junctions. (Barthenschlager, et al., 1993. *J. Virol.* 67, 3835-3844, Grakoui, et al., 1993. *Proc. Natl. Acad. Sci. USA* 90, 10583-10587, Tomei, et al., 1993. *J. Virol.* 67, 4017-4026.) NS4A provides a cofactor for NS3 activity. (Failla, et al., *J. Virol.* 1994. 68, 3753-3760, De Francesco, et al., U.S. Pat. No. 5,739,002.) NS5A is a highly phosphorylated protein concurring interferon resistance. (De Francesco, et al., 2000. *Semin Liver Dis.*, 20(1), 69-83, Pawlotsky, 1999. *J. Viral Hepat. Suppl.* 1, 47-48.) NS5B provides an RNA polymerase. (De Francesco, et al., International Publication Number WO 96/37619, Behrens, et al., 1996. *EMBO* 15, 12-22, Lohmann, et al., 1998. *Virology* 249, 108-118.)

Lohmann, et al., *Science* 285, 110-113, 1999, illustrates the ability of a biscistronic HCV replicon to replicate in a hepatoma cell line. The biscistonic HCV replicon contained a neomycin cistron and an NS2-NS5B or an NS3-NS5B cistron. "NS2-NS5B" refers to a NS2-NS3-NS4A-NS4B-NS5A-NS5B polyprotein. "NS3NS5B" refers to a NS3-NS4A-NS4B-NS5A-NS5B polyprotein.

Bartenschlager, European Patent Application 1 043 399, published Oct. 11, 2000 (not admitted to be prior art to the claimed invention), describes a cell culture system for autonomous HCV RNA replication and protein expression. Replication and protein expression is indicated to occur in sufficiently large amounts for quantitative determination. European Patent Application 1 043 399 indicates that prior cell lines or primary cell cultures infected with HCV do not provide favorable circumstances for detecting HCV replication.

SUMMARY OF THE INVENTION

The present invention features nucleic acid containing one or more adaptive mutations, and HCV replicon enhanced cells. Adaptive mutations are mutations that enhance HCV replicon activity. HCV replicon enhanced cells are cells having an increased ability to maintain an HCV replicon.

An HCV replicon is an RNA molecule able to autonomously replicate in a cultured cell and produce detectable levels of one or more HCV proteins. The basic subunit of an HCV replicon encodes for a HCV NS3-NS5B polyprotein along with a suitable 5' UTR-partial core (PC) region and 3' UTR. The 5' UTR-PC region is made up of a 5' UTR region and about 36 nucleotides of the beginning of the core. Additional regions may be present including those coding for HCV proteins or elements such as the complete core, E1, E2, p7 or NS2; and those coding for other types of proteins or elements such as a encephalomyocarditis virus (EMCV) internal ribosome entry site (IRES), a reporter protein or a selection protein.

The present application identifies different adaptive mutations that enhance HCV replicon activity. Enhancing replicon activity brings about at least one of the following: an increase in replicon maintenance in a cell, an increase in replicon replication, and an increase in replicon protein expression.

Adaptive mutations are described herein by identifying the location of the adaptive mutation with respect to a reference sequence present in a particular region. Based on the provided reference sequence, the same adaptive mutation can be produced in corresponding locations of equivalent regions having an amino acid sequence different than the reference sequence. Equivalent regions have the same function or encode for a polypeptide having the same function.

Replicon enhanced cells are a preferred host for the insertion and expression of an HCV replicon. Replicon enhanced cells are initially produced by creating a cell containing a HCV replicon and then curing the cell of the replicon. The term "replicon enhanced cell" includes cells cured of HCV replicons and progeny of such cells.

Thus, a first aspect of the present invention describes a nucleic acid molecule comprising at least one of the following regions: an altered NS3 encoding region, an altered NS5A encoding region, and an altered EMCV IRES region. The altered region contains one or more adaptive mutations. Reference to the presence of particular adaptive mutation(s) does not exclude other mutations or adaptive mutations from being present. Adaptive mutations are described with reference to either an encoded amino acid sequence or a nucleic acid sequence.

A nucleic acid molecule can be single-stranded or part of a double strand, and can be RNA or DNA. Depending upon the structure of the nucleic acid molecule, the molecule may be used as a replicon or in the production of a replicon. For example, single-stranded RNA having the proper regions can be a replicon, while double-stranded DNA that includes the complement of a sequence coding for a replicon or replicon intermediate may useful in the production of the replicon or replicon intermediate.

Preferred nucleic acid molecules are those containing region(s) from SEQ. ID. NOs. 1, 2, or 3, or the RNA version thereof, with one or more adaptive mutations. Reference to "the RNA version thereof" indicates a ribose backbone and the presence of uracil instead of thymine.

The presence of a region containing an adaptive mutation indicates that at least one such region is present. In different embodiments, for example, adaptive mutations described herein are present at least in the NS3 region, in the NS5A region, in the NS3 and NS5A regions, in the EMCV IRES and NS3 regions, in the EMCV and NS5A regions, and in the ECMV IRES, NS3 and NS5A regions.

Another aspect of the present invention describes an expression vector comprising a nucleotide sequence of an HCV replicon or replicon intermediate coupled to an exogenous promoter. Reference to a nucleotide sequence "coupled to an exogenous promoter" indicates the presence and positioning of an RNA promoter such that it can mediate transcription of the nucleotide sequence and that the promoter is not naturally associated with the nucleotide sequence being transcribed. The expression vector can be used to produce RNA replicons.

Another aspect of the present invention describes a recombinant human hepatoma cell. Reference to a recombinant cell includes an initially produced cell and progeny thereof.

Another aspect of the present invention describes a method of making a HCV replicon enhanced cell. The method involves the steps of: (a) introducing and maintaining an HCV replicon into a cell and (b) curing the cell of the HCV replicon.

Another aspect of the present invention describes an HCV replicon enhanced cell made by a process comprising the steps of: (a) introducing and maintaining an HCV replicon into a cell and (b) curing the cell of the HCV replicon.

Another aspect of the present invention describes a method of making a HCV replicon enhanced cell comprising an HCV replicon. The method involves (a) introducing and maintaining a first HCV replicon into a cell, (b) curing the cell of the replicon, and (c) introducing and maintaining a second replicon into the cured cell, where the second replicon may be the same or different as the first replicon.

Another aspect of the present invention describes an HCV replicon enhanced cell containing a HCV replicon made by the process involving the step of introducing an HCV replicon into an HCV replicon enhanced cell. The HCV replicon introduced into the HCV replicon enhanced cell may be the same or different than the HCV replicon used to produce the HCV replicon enhanced cell. In a preferred embodiment, the HCV replicon introduced into an HCV replicon enhanced cell is the same replicon as was used to produce the enhanced cell.

Another aspect of the present invention describes a method of measuring the ability of a compound to affect HCV activity using an HCV replicon comprising an adaptive mutation described herein. The method involves providing a compound to a cell comprising the HCV replicon and measuring the ability of the compound to affect one or more replicon activities as a measure of the effect on HCV activity.

Another aspect of the present invention describes a method of measuring the ability of a compound to affect HCV activity using an HCV replicon enhanced cell that comprises an HCV replicon. The method involves providing a compound to the cell and measuring the ability of the compound to effect one or more replicon activities as a measure of the effect on HCV activity.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF SEQ ID NO: 3

The nucleic acid sequence for the pHCVNeo.17 coding strand is provided by SEQ ID NO: 3. The different regions of pHCVNeo.17 are provided as follows:
1-341: HCV 5' non-translated region, drives translation of the core-neo fusion protein;
342-1181: Core-neo fusion protein, selectable marker;
1190-1800: Internal ribosome entry site of the encephalomyocarditis virus, drives translation of the HCV NS region;
1801-7755: HCV polyprotein from non-structural protein 3 to non-structural protein 5B;
1801-3696: Non-structural protein 3 (NS3), HCV NS3 protease/helicase;
3697-3858: Non-structural protein 4A (NS4A), NS3 protease cofactor;
3859-4641: Non-structural protein 4B (NS4B);
4642-5982: Non-structural protein 5A (NS5A);
5983-7755: Non-structural protein 5B (NS5B); RNA-dependent RNA polymerase
7759-7989: HCV 3' non-translated region; and
7990-10690 plasmid sequences comprising origin of replication, beta lactamase coding sequence, and T7 promoter.

DETAILED DESCRIPTION OF THE INVENTION

HCV replicons and HCV replicon enhanced cells can be used to produce a cell culture providing detectable levels of HCV RNA and HCV protein. HCV replicons and HCV replicon enhanced hosts can both be obtained by selecting for the ability to maintain an HCV replicon in a cell. As illustrated in the examples provided below, adaptive mutations present in HCV replicons and host cells can both assist replicon maintenance in a cell.

The detectable replication and expression of HCV RNA in a cell culture system has a variety of different uses including being used to study HCV replication and expression, to study HCV and host cell interactions, to produce HCV RNA, to produce HCV proteins, and to provide a system for measuring the ability of a compound to modulate one or more HCV activities.

Preferred cells for use with a HCV replicon are Huh-7 cells and Huh-7 derived cells. "Huh-7 derived cells" are cell produced starting with Huh-7 cells and introducing one or more phenotypic and/or genotypic modifications.

Adaptive Mutations

Adaptive mutations enhance the ability of an HCV replicon to be maintained and expressed in a host cell. Adaptive mutations can be initially selected for using a wild type HCV RNA construct or a mutated HCV replicon. Initial selection involves providing HCV replicons to cells and identifying clones containing a replicon.

Nucleic acid sequences of identified HCV replicons can be determined using standard sequencing techniques. Comparing the sequence of input HCV constructs and selected constructs provides the location of mutations. The effect of particular mutation(s) can be measured by, for example, producing a construct to contain particular mutation(s) and measuring the effect of these mutation(s). Suitable control constructs for comparison purposes include wild type constructs and constructs previously evaluated.

Adaptive mutations were predominantly found in the HCV NS3 and NS5A regions. With the exception of two silent mutations in NS5A and NS5B, consensus mutations occurring in the NS region resulted in changes to the deduced amino acid sequence. Noticeably, the amino acid changes occurred in residues that are conserved in all or a large number of natural HCV isolates. HCV sequences are well known in the art and can be found, for example, in GenBank.

Adaptive mutations described herein can be identified with respect to a reference sequence. The reference sequence provides the location of the adaptiv mutation in, for example, the NS3 or NS5A RNA, cDNA, or amino acid sequence. The remainder of the sequence encodes for a functional protein that may have the same, or a different, sequence than the reference sequence.

Preferred NS3 and NS5A adaptive mutations and examples of changes that can be made to produce such mutations are shown in Tables 1 and 2. The amino acid numbering shown in Tables 1 and 2 is with respect to SEQ. ID. NO. 1. The nucleotide numbering shown in Tables 1 and 2 is with respect to SEQ. ID. NO. 2. SEQ. ID. NO. 1 provides the amino acid sequence of the Con 1 HCV isolate (Accession Number AJ238799). SEQ. ID. NO. 2 provides the nucleic acid sequence of the Con1 HCV isolate.

TABLE 1

Preferred NS3 Adaptive Mutations

| Amino Acid | Nucleotide |
|---|---|
| gly1095ala | G3625C |
| glu1202gly | A3946G |
| ala1347thr | G4380A |

TABLE 2

Preferred NS5A Adaptive Mutations

| Amino Acid | Nucleotide |
|---|---|
| Lys@2039 | AAA@6458 |
| asn2041thr | A6463C |
| ser2173phe | C6859T |
| ser2197phe | C6931T |
| leu2198ser | T6934C |
| ala2199thr | G6936A |
| ser2204arg | C6953A (or G) |

@refers to an addition.

Preferred adaptive mutations identified with respect to a reference sequence can be produced changing the encoding region of SEQ. ID. NO. 1, or an equivalent sequence, to result in the indicated change. Preferred adaptive mutations provided in Tables 1 and 2 occur in amino acids conserved among different HCV isolates.

Adaptive mutations have different effects. Some mutations alone, or in combination with other mutations, enhance HCV replicon activity. In some cases, two or more mutations led to synergistic effects and in one case, a slightly antagonistic effect was observed.

An adaptive mutation once identified can be introduced into a starting construct using standard genetic techniques. Examples of such techniques are provided by Ausubel, *Current Protocols in Molecular Biology*, John Wiley, 1987-1998, and Sambrook, et al., *Molecular Cloning, A Laboratory Manual*, 2$^{nd}$ Edition, Cold Spring Harbor Laboratory Press, 1989.

HCV replicons containing adaptive mutations can be built around an NS3 region or NS5A region containing one or more adaptive mutations described herein. The final replicon will contain replicon components needed for replication and may contain additional components.

SEQ. ID. NO. 2 can be used as a reference point for different HCV regions as follows:
5' UTR-nucleotides 1-341;
Core-nucleotides 342-914;
E1-nucleotides 915-1490;
E2-nucleotides 1491-2579;
P7-nucleotides 2580-2768;
NS2-nucleotides 2769-3419;
NS3-nucleotides 3420-5312;
NS4A-nucleotides 5313-5474;
NS4B-nucleotides 5475-6257;
NS5A-nucleotides 6258-7598;
NS5B-nucleotides 7599-9371; and
3' UTR-nucleotides 9374-9605.
The amino acid sequences of the different structural and non-structural regions is provided by SEQ. ID. NO. 1.

Nucleic acid sequences encoding for a particular amino acid can be produced taking into account the degeneracy of the genetic code. The degeneracy of the genetic code arises because almost all amino acids are encoded for by different combinations of nucleotide triplets or "codons". The translation of a particular codon into a particular amino acid is well known in the art (see, e.g., Lewin *GENES IV*, p. 119, Oxford University Press, 1990). Amino acids are encoded for by RNA codons as follows:
A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Set=Serine: codons AGC, AGU, UCA, UCC, UCG, UCU
T=Thr-Threonine: codons ACA, ACC, ACG, ACU
V=Val=Valine: codons GUA, GUC, GUG, GUU
W=Trp=Tryptophan: codon UGG
Y=Tyr-Tyrosine: codons UAC, UAU.

Constructs, including subgenomic and genomic replicons, containing one or more of the adaptive mutations described herein can also contain additional mutations. The additional mutations may be adaptive mutations and mutations not substantially inhibiting replicon activity. Mutations not substantially inhibiting replicon activity provide for a replicon that can be introduced into a cell and have detectable activity.

HCV Replicon

HCV replicons include the full length HCV genome and subgenomic constructs. A basic HCV replicon is a subgenomic construct containing an HCV 5' UTR-PC region, an HCV NS3-NS5B polyprotein encoding region, and a HCV 3' UTR. Other nucleic acid regions can be present such as those providing for HCV NS2, structural HCV protein(s) and non-HCV sequences.

The HCV 5' UTR-PC region provides an internal ribosome entry site (IRES) for protein translation and elements needed for replication. The HCV 5' UTR-PC region includes naturally occurring HCV 5' UTR extending about 36 nucleotides into a HCV core encoding region, and functional derivatives thereof. The 5'-UTR-PC region can be present in different locations such as site downstream from a sequence encoding a selection protein, a reporter, protein, or an HCV polyprotein.

Functional derivatives of the 5'-UTR-PC region able to initiate translation and assist replication can be designed taking into structural requirements for HCV translation initiation. (See, for example, Honda, et al., 1996. *Virology* 222, 31-42). The affect of different modifications to a 5' UTR-PC region can be determined using techniques that measure replicon activity.

In addition to the HCV 5' UTR-PC region, non-HCV IRES elements can also be present in the replicon. The non-HCV IRES elements can be present in different locations including immediately upstream the region encoding for an HCV polyprotein. Examples of non-HCV IRES elements that can be used are the EMCV IRES, poliovirus IRES, and bovine viral diarrhea virus IRES.

The HCV 3' UTR assists HCV replication. HCV 3' UTR includes naturally occurring HCV 3' UTR and functional derivatives thereof. Naturally occurring 3' UTR's include a poly U tract and an additional region of about 100 nucleotides. (Tanaka, et al., 1996. *J. Virol.* 70, 3307-3312, Kolykhalov, et aL, 1996. *J. Virol.* 70, 3363-3371.) At least in vivo, the 3' UTR appears to be essential for replication. (Kolykhalov, et al., 2000. *J. Virol.* 2000 4, 2046-2051.) Examples of naturally occurring 3' UTR derivatives are described by Bartenschlager International Publication Number EP 1 043 399.

The NS3-NS5B polyprotein encoding region provides for a polyprotein that can be processed in a cell into different proteins. Suitable NS3-NS5B polyprotein sequences that may be part of a replicon include those present in different HCV strains and functional equivalents thereof resulting in the processing of NS3-NS5B to a produce functional replication machinery. Proper processing can be measured for by assaying, for example, NS5B RNA dependent RNA polymerase.

The ability of an NS5B protein to provide RNA polymerase activity can be measured using techniques well known in the art. (See, for example, De Franscesco, et al., International Publication Number WO 96/37619, Behrens, et al., 1996. *EMBO* 15:12-22, Lohmann, et al., 1998. *Virology* 249:108-118.) Preferably, the sequence of the active NS5B is substantially similar as that provided in SEQ. ID. NO. 1, or a wild type NS5B such as strains HCV-1, HCV-2, HCV-BK, HCV-J, HCV-N, HCV-H. A substantially similar sequence provides detectable HCV polymerase activity and contains 1, 2, 3, 4, 5, 6, 7, 8, 9, 10, 11, 12, 13, 14, or 15 amino acid alterations to that present in a HCV NS5B polymerase. Preferably, no more than 1, 2, 3, 4 or 5 alterations are present.

Alterations to an amino acid sequence provide for substitution(s), insertion(s), deletion(s) or a combination thereof. Sites of different alterations can be designed taking into account the amino acid sequences of different NS5B polymerases to identify conserved and variable amino acid, and can be empirically determined.

HCV replicons can be produced in a wide variety of different cells and in vitro. Suitable cells allow for the transcription of a nucleic acid encoding for an HCV replicon.

Additional Sequences

An HCV replicon may contain non-HCV sequences in addition to HCV sequences. The additional sequences should not prevent replication and expression, and preferably serve a useful function. Sequences that can be used to serve a useful function include a selection sequence, a reporter sequence, transcription elements and translation elements.

Selection Sequence

A selection sequence in an HCV replicon facilitates the identification of a cell containing the replicon. Selection sequences are typically used in conjunction with some selective pressure that inhibits growth of cells not containing the selection sequence. Examples of selection sequences include sequences encoding for antibiotic resistance and ribozymes.

Antibiotic resistance can be used in conjunction with an antibiotic to select for cells containing replicons. Examples of selection sequences providing for antibiotic resistance are sequences encoding resistance to neomycin, hygromycin, puromycin, or zeocin.

A ribozyme serving as a selection sequence can be used in conjunction with an inhibitory nucleic acid molecule that prevents cellular growth. The ribozyme recognizes and cleaves the inhibitory nucleic acid.

Reporter Sequence

A reporter sequence can be used to detect replicon replication or protein expression. Preferred reporter proteins are enzymatic proteins whose presence can be detected by measuring product produced by the protein. Examples of reporter proteins include, luciferase, beta-lactamase, secretory alkaline phosphatase, beta-glucuronidase, green fluorescent protein and its derivatives. In addition, a reporter nucleic acid sequence can be used to provide a reference sequence that can be targeted by a complementary nucleic acid. Hybridization of the complementary nucleic acid to its target can be determined using standard techniques.

Additional Sequence Configuration

Additional non-HCV sequences are preferable 5' or 3' of an HCV replicon genome or subgenomic genome region. However, the additional sequences can be located within an HCV genome as long as the sequences do not prevent detectable replicon activity. If desired, additional sequences can be separated from the replicon by using a ribozyme recognition sequence in conjunction with a ribozyme.

Additional sequences can be part of the same cistron as the HCV polyprotein or can be a separate cistron. If part of the same cistron, the selection or reporter sequence coding for a protein should result in a product that is either active as a chimeric protein or is cleaved inside a cell so it is separated from HCV protein.

Selection and reporter sequences encoding for a protein when present as a separate cistron should be associated with elements needed for translation. Such elements include a 5' IRES.

Detection Methods

Methods for detecting replicon activity include those measuring the production or activity of replicon RNA and encoded for protein. Measuring includes qualitative and quantitative analysis.

Techniques suitable for measuring RNA production include those detecting the presence or activity of RNA. The presence of RNA can be detected using, for example, complementary hybridization probes or quantitative PCR. Techniques for measuring hybridization between complementary nucleic acid and quantitative PCR are well known in the art. (See for example, Ausubel, *Current Protocols in Molecular Biology*, John Wiley, 1987-1998, Sambrook, et al., *Molecular Cloning, A Laboratory Manual*, $2^{nd}$ Edition, Cold Spring Harbor Laboratory Press, 1989, and U.S. Pat. No. 5,731,148.)

RNA enzymatic activity can be provided to the replicon by using a ribozyme sequence. Ribozyme activity can be measured using techniques detecting the ability of the ribozyme to cleave a target sequence.

Techniques for measuring protein production include those detecting the presence or activity of a produced protein. The presence of a particular protein can be determined by, for example, immunological techniques. Protein activity can be measured based on the activity of an HCV protein or a reporter protein sequence.

Techniques for measuring HCV protein activity vary depending upon the protein that is measured. Techniques for measuring the activity of different nonstructural proteins such as NS2/3, NS3, and NS5B, are well known in the art. (See, for example, references provided in the Background of the Invention.)

Assays measuring replicon activity also include those detecting virion production from a replicon that produces a virion; and those detecting a cytopathic effect from a replicon producing proteins exerting such an effect. Cytopathic effects can be detected by assays suitable to measure cell viability.

Assays measuring replicon activity can be used to evaluate the ability of a compound to modulate HCV activities. Such assays can be carried out by providing one or more test compounds to a cell expressing an HCV replicon and measuring the effect of the compound on replicon activity. If a preparation containing more than one compound is found to modulate replicon activity, individual compounds or smaller groups of compounds can be tested to identify replicon active compounds.

Compounds identified as inhibiting HCV activity can be used to produce replicon enhanced cells and may be therapeutic compounds. The ability of a compound to serve as a therapeutic compound can be confirmed using animal models such as a chimpanzee to measure efficacy and toxicity.

Replicon Enhanced Host Cell

Replicon enhanced cells are initially produced by selecting for a cell able to maintain an HCV replicon and then curing the cell of the replicon. Cells produced in this fashion were found to have an increased ability to maintain a replicon upon subsequent HCV replicon transfection.

Initial transfection can be performed using a wild-type replicon or a replicon containing one or more adaptive mutations. If a wild-type replicon is employed, the replicon should contain a selection sequence to facilitate replicon maintenance.

Cells can be cured of replicons using different techniques such as those employing replicon inhibitory agent. In addition, replication of HCV replicons is substantially reduced in confluent cells. Thus, it is conceivable to cure cells of replicons by culturing them at a high density.

Replicon inhibitory agents inhibit replicon activity or select against a cell containing a replicon. An example of such an agent is IFN-α. Other HCV inhibitory compounds may also be employed. HCV inhibitor compounds are described, for example, in Llinas-Brunet, et al., 2000. *Bioorg Med Chem. Lett*. 10(20), 2267-2270.

The ability of a cured cell to be a replicon enhanced cell can be measured by introducing a replicon into the cell and determining efficiency of subsequent replicon maintenance and activity.

EXAMPLES

Examples are provided below to further illustrate different features of the present invention. The examples also illustrate useful methodology for practicing the invention. These examples do not limit the claimed invention.

Example 1

Techniques

This example illustrates the techniques employed for producing and analyzing adaptive mutations and replicon enhanced cells.

Manipulation of Nucleic Acids and Construction of Recombinant Plasmids

Manipulation of nucleic acids was done according to standard protocols. (Sambrook, et al., 1989. *Molecular Cloning: A Laboratory Manual*, $2^{nd}$ ed. Cold Spring Harbor Laboratory, Cold Spring Harbor, N.Y.) Plasmid DNA was prepared from ON culture in LB broth using Qiagen 500 columns according to manufacturer instructions.

Plasmids containing desired mutations were constructed by restriction digestion using restriction sites flanking the mutations or by PCR amplification of the area of interest, using synthetic oligonucleotides with the appropriate sequence. Site directed mutagenesis was carried out by inserting the mutations in the PCR primers. PCR amplification was performed using high fidelity thermostable polymerases or mixtures of polymerases containing a proofreading enzyme. (Barnes, et al., 1994. *Proc. Natl. Acad. Sci*. 91, 2216-2220.) All plasmids were verified by restriction mapping and sequencing.

pHCVneo17.wt contains the cDNA for an HCV bicistronic replicon identical to replicon $I_{377}$neo/NS3-3'/wt described by Bartenschlager (SEQ. ID. NO. 3) (Lohmann, et al., 1999. *Science* 285,110-113, EMBL-genbank No. AJ242652). The plasmid comprises the following elements: 5' untranslated region of HCV comprising the HCV-IRES and part of the core (nt1-377); neomycin phosphotransferase coding sequence; and EMCV IRES; HCV coding sequences from NS3 to NS5B; 3' UTR of HCV.

Plasmid pHCVNeo17.GAA is identical to pHCVneo.17, except that the GAC triplets (nt. 6934-6939 of pHCVNeo17 sequence) coding for the catalytic aspartates of the NS5B polymerase (amino acids 2737 and 2738 of HCV polyprotein) were changed into GCG, coding for alanine.

Plasmid pHCVNeo17.m0 is identical to pHCVNeo17, except that the triplet AGC (nt. 5335-5337 of pHCVNeo17 sequence) coding for the serine of NS5A protein (amino acid 2204 of HCV polyprotein) was changed into AGA, coding for arginine.

Plasmid pHCVNeo17.m1 is identical to pHCVNeo17, except that the triplet AAC (nt. 4846-4848 of pHCVNeo17 sequence) coding for the asparagine of NS5A protein (amino acid 2041 of HCV polyprotein) was changed into ACC, coding for threonine.

Plasmid pHCVNeo17.m2 is identical to pHCVNeo17, except that the triplet TCC (nt. 5242-5244 of pHCVNeo17 sequence) coding for the serine of NS5A protein (amino acid 2173 of HCV polyprotein) was changed into TTC, coding for phenylalanine.

Plasmid pHCVNeo17.m3 is identical to pHCVNeo17, except that the triplet TCC (nt. 5314-5316 of pHCVNeo17 sequence) coding for the serine of NS5A protein (amino acid 2197 of HCV polyprotein) was changed into TTC, coding for phenylalanine.

Plasmid pHCVNeo17.m4 is identical to pHCVNeo17, except that the triplet TTG (nt. 5317-5319 of pHCVNeo17 sequence) coding for the leucine of NS5A protein (amino acid 2198 of HCV polyprotein) was changed into TCG, coding for serine.

Plasmid pHCVNeo17.m5 is identical to pHCVNeo17, except that an extra triplet AAA coding for lysine was inserted after the triplet GTG (nt. 4840-4843 of pHCVNeo17 sequence), coding for valine 2039 of HCV polyprotein. Plasmid pHCVNeo17.m6 is identical to pHCVNeo17, except that the triplets GAA and GCC (nt. 2329-2331 and 2764-2766 of pHCVNeo17 sequence) coding for the glutamic acid and the alanine of NS3 protein (amino acid 1202 and 1347 of HCV polyprotein) were changed respectively into GGA and ACC, coding for glycine and threonine. The triplet TCC (nt. 5242-5244 of pHCVNeo17 sequence) coding for the serine of NS5A protein (amino acid 2173 of HCV polyprotein) was changed into TTC, coding for phenylalanine; an extra adenosine was inserted into the EMCV TRES (after the thymidine 1736 of the replicon sequence).

Plasmid pHCVNeo17.m7 is identical to pHCVNeo17, except that the triplet AAC (nt. 4846-4848 of pHCVNeo17 sequence) coding for the asparagine of NS5A protein (amino acid 2041 of HCV polyprotein) was changed into ACC, coding for threonine; the triplet TCC (nt. 5242-5244 of pHCV-Neo17 sequence) coding for the serine of NS5A protein (amino acid 2173 of HCV polyprotein) was changed into TTC, coding for phenylalanine.

Plasmid pHCVNeo17.m8 is identical to pHCVNeo17, except that the triplet AAC (nt. 4846-4848 of pHCVNeo17 sequence) coding for the asparagine of NS5A protein (amino acid 2041 of HCV polyprotein) was changed into ACC, coding for threonine; the triplet TCC (nt. 5314-5316 of pHCV-Neo 17 sequence) coding for the serine of NS5A protein (amino acid 2197 of HCV polyprotein) was changed into TTC, coding for phenylalanine.

Plasmid pHCVNeo17.m9 is identical to pHCVNeo17, except that the triplet AAC (nt. 4846-4848 of pHCVNeo17 sequence) coding for the asparagine of NS5A protein (amino acid 2041 of HCV polyprotein) was changed into ACC, coding for threonine; the triplet TTG (nt. 5317-5319 of pHCV-Neo17 sequence) coding for the leucine of NS5A protein (amino acid 2198 of HCV polyprotein) was changed into TCG, coding for serine.

Plasmid pHCVNeo17.m10 is identical to pHCVNeo17, except that the triplet GAA (nt. 2329-2331 of pHCVNeo17 sequence) coding for the glutamic acid of NS3 protein (amino acid 1202 of HCV polyprotein) was changed into GGA, coding for glycine; an extra triplet AAA coding for lysine was inserted after the triplet GTG (nt. 4840-4843 of pHCVNeo17 sequence), coding for valine 2039 of HCV polyprotein.

Plasmid pHCVNeo17.m11 is identical to pHCVNeo17, except that the triplet TCC (nt. 5314-5316 of pHCVNeo17 sequence) coding for the serine of NS5A protein (amino acid 2197 of HCV polyprotein) was changed into TTC, coding for phenylalanine. The triplet GCC (nt. 5320-5322 of pHCV-Neo17 sequence) coding for the alanine of NS5A protein (amino acid 2199 of HCV polyprotein) was changed into ACC coding for threonine.

Plasmid pHCVNeo17.m12 is identical to pHCVNeo17, except that the triplet AAC (nt. 4846-4848 of pHCVNeo17 sequence) coding for the asparagine of NS5A protein (amino acid 2041 of HCV polyprotein) was changed into ACC, coding for threonine; the triplet TCC (nt. 5314-5316 of pHCV-Neo17 sequence) coding for the serine of NS5A protein (amino acid 2197 of HCV polyprotein) was changed into TTC, coding for phenylalanine. The triplet GCC (nt. 5320-5322 of pHCVNeo17 sequence) coding for the alanine of NS5A protein (amino acid 2199 of HCV polyprotein) was changed into ACC coding for threonine.

Plasmid pHCVNeo17.m13 has the same mutations as pHCVNeo17.m8, but also an extra adenosine inserted into the EMCV IRES (after the thymidine 1736 of the replicon sequence).

Plasmid pHCVNeo17.m14 has the same mutations as pHCVNeo17.m11, but also an extra adenosine inserted into the EMCV IRES (after the thymidine 1736 of the replicon sequence).

Plasmid pHCVNeo17.m15 is identical to pHCVNeo17, except that the triplet GCC (nt. 5320-5322 of pHCVNeo17 sequence) coding for the alanine of NS5A protein (amino acid 2199 of HCV polyprotein) was changed into ACC coding for threonine.

Plasmid pRBSEAP.5 is a pHCVNeo.17 derivative where the Neo coding sequence has been replaced with the sequence coding for the human placental alkaline phosphatase corresponding to nucleotides 90-1580 of pBC12/RSV/SEAP plasmid. (Berger, et al., 1988. *Gene* 66, 1-10.)

RNA Transfection

Transfection was performed using Huh-7 cells. The cells were grown in Dulbecco's modified minimal essential medium (DMEM, Gibco, BRL) supplemented with 10% FCS. For routine work, cells were passed 1 to 5 twice a week using 1× trypsin/EDTA (Gibco, BRL).

Plasmids were digested with the ScaI endonuclease (New England Biolabs) and transcribed in vitro with the T7 Megascript kit (Ambion). Transcription mixtures were treated with DNase I(0.1 U/ml) for 30 minutes at 37° C. to completely remove template DNA, extracted according to the procedure of Chomczynski (Chomczynski, et al., 1987. *Anal. Biochem.* 162, 156-159), and resuspended with RNase-free phosphate buffered saline (rfPBS, Sambrook, et al., 1989. *Molecular Clotting: A Laboratory Manual*, $2^{nd}$ ed. Cold Spring Harbor Laboratory, Cold Spring Harbor, N.Y.).

RNA transfection was performed as described by Liljestrom, et al., 1991. *J. Virol.* 6, 4107-4113, with minor modifications. Subconfluent, actively growing cells were detached from the tissue culture container using trypsin/EDTA. Trypsin was neutralised by addition of 3 to 10 volumes of DMEM/10% FCS and cells were centrifuged for 5 minutes at 1200 rpm in a Haereus table top centrifuge at 4° C. Cells were resuspended with ice cold rfPBS by gentle pipetting, counted with a haemocitometer, and centrifuged as above. rfPBS wash was repeated once and cells were resuspended at a concentration of 1-2×$10^7$ cell/ml in rfPBS. Aliquots of cell suspension were mixed with RNA in sterile eppendorf tubes. The RNA/cell mixture was immediately transferred into the electroporation cuvette (precooled on ice) and pulsed twice with a gene pulser apparatus equipped with pulse controller (Biorad). Depending on the experiment, 0.1, 0.2 or 0.4 cm electrode gap cuvettes were used, and settings adjusted (Table 3).

TABLE 3

| Cuvette gap (cm) | Volume (µl) | Voltage (Volts) | Capacitance (µFa) | Resistance (ohm) | RNA (µg) |
|---|---|---|---|---|---|
| 0.1 | 70 | 200 | 25 | infinite | 1-10 |
| 0.2 | 200 | 400 | 25 | infinite | 5-20 |
| 0.4 | 800 | 800 | 25 | infinite | 15-100 |

After the electric shock, cells were left at room temperature for 1-10 minutes (essentially the time required to electroporate all samples) and subsequently diluted with at least 20 volumes of DMEM/10% FCS and plated as required for the experiment. Survival and transfection efficiency were monitored by measuring the neutral red uptake of cell cultured for various days in the absence or in the presence of neomycin sulfate (G418). With these parameters, survival of Huh-7 cells was usually 40-60% and transfection efficiency ranged between 40% and 100%.

Sequence Analysis of Replicon RNAs

The entire NS region was recloned from 3 different transfection experiments performed with HCVNeo.17 RNA. RNA was extracted from selected clones either using the Qiagen RNAeasy minikit following manufacturer instructions or as described by Chomczynski, et al., 1987. Anal. Biochem. 162, 156-159.

Replicon RNAs (5 μg of total cellular RNA) were retrotranscribed using oligonucleotide HCVG34 (5'-ACATGATCTGCAGAGAGGCCAGT-3'; SEQ. ID. No. 4) and the Superscript II reverse transcriptase (Gibco, BRL) according to manufacturer instructions, and subsequently digested with 2 U/ml Ribonuclease H (Gibco BRL). The cDNA regions spanning from the EMCV IRES to the HCV 3' end were amplified by PCR using oligonucleotides HCVG39 (5'-GACASGCTGTGATAWATGTCTCCCCC-3'; SEQ. ID. NO. 5) and CITE3 (5'-TGGCTCTCCTCAAGCGTATTC-3'; SEQ. ID. NO. 6) and the LA Taq DNA polymerase (Takara LA Taq).

Amplified cDNAs were digested with the KpnI end endouclease (New England Biolabs) and the 5.8 kb fragments were gel purified and ligated to the 5.6 kb vector fragment (purified from plasmid pRBSEAP.5 digested with Kpnl) using T4 DNA ligase (New England Biolabs) according to manufacturer instructions. Ligated DNAs were transformed by electroporation in DH10B or JM119 strains of *E. coli*.

In the case of NS5A region, total RNA isolated from 3 clones, (HB77, HB60 and HB68) was extracted and used for RT-PCR. 5 μg of total RNA plus 20 pmole of AS61 oligo (5'-ACTCTCTGCAGTCAAGCGGCTCA-3', RT antisense oligo; SEQ. ID. NO. 7) were heated 5 minutes at 95° C., then DMSO (5% f.c.), DTT (10 mM f.c.), 1 mM dNTP (1 mM f.c.), 1× Superscript buffer (1×f.c.), and 10 μSuperscript (Gibco) were added to a total volume of 20 μl and incubated 3 hours at 42° C. 2 μl of this RT reaction were used to perform PCR with oligos S39 (5'-CAGTGGATGAACCGGCTGATA-3', sense; SEQ. ID. NO. 8) or S41 (5'-GGGGCGACGGCATCATG-CAAACC-3', sense; SEQ. ID. NO. 9) and B43 (5'-CAGGAC-CTGCAGTCTGTCAAAGG-3', antisense; SEQ. ID. NO. 10) using Elongase Enzyme Mix (Gibco) according the instruction provided by the manufacturer. The resulting PCR fragment was cloned in pCR2.1 vector using the TA Cloning kit (Invitrogen) and transformed in Top10F' bacterial strain.

Plasmid DNA was prepared from ON culture of the resulting ampicillin resistant colonies using Qiagen 500 columns according to manufacturer instructions. The presence of the desired DNA insert was ascertained by restriction digestion, and the nucleotide sequence of each plasmid was determined by automated sequencing. Nucleotide sequences and deduced amino acids sequences were aligned using the GCG software.

TaqMan

TaqMan analysis was typically performed using 10 ng of RNA in a reaction mix (TaqMan Gold RT-PCR kit, Perkin Elmer Biosystems) either with HCV specific oligos/probe (oligo 1: 5'-CGGGAGAGCCATAGTGG-3'; SEQ. ID. NO. 11, oligo 2: 5'-AGTACCACAAGGCCTTTCG-3'; SEQ. ID. NO. 12, probe: 5'-CTGCGGAACCGGTGAGTACAC-3'; SEQ. ID. NO. 13) or with human GAPDH specific oligos/probe (Pre-Developed TaqMan Assay Reagents, Endogenous Control Human GAPDH, Part Number 4310884E, Perkin Elmer Biosystems). PCR was performed using a Perkin Elmer ABI PRISM 7700 under the following conditions: 30 minutes at 48° C. (the RT step), 10 minutes at 95° C. and 40 cycles: 15 seconds at 95° C. and 1 minute at 60° C. Quantitative calculations were obtained using the Comparative $C_T$ Method (described in User Bulletin #2, ABI PRISM 7700 Sequence Detection System, Applied Biosystem, December 1997) considering the level of GAPDH mRNA constant. All calculations of HCV RNA are expressed as fold difference over a specific control.

Antibodies and Immunological Techniques

Mouse monoclonal antibody (anti-NS3 mab10E5/24) were produced by standard techniques. (Galfré and Milstein, 1981. *Methods in Enzymology* 73, 1-46.) Purified recombinant protein was used as an immunogen. (Gallinari, et al., 1999. *Biochemistry* 38, 5620-5632.)

For Cell-ELISA analysis, transfected cells were monitored for expression of the NS3 protein by ELISA with the anti-NS3 mab 10E5/24. Cells were seeded into 96 well plates at densities of 40,000, 30,000, 15,000 and 10,000 cells per well and fixed with ice-cold isopropanol at 1, 2, 3 and 4 days post-transfection, respectively. The cells were washed twice with PBS, blocked with 5% non-fat dry milk in PBS +0.1% Triton X100 +0.02% SDS (PBSTS) and then incubated overnight at 4° C. with 10E5/24 mab diluted 1:2000 in Milk/PBSTS. After washing 5 times with PBSTS, the cells were incubated for 3 hours at room temperature with anti-mouse IgG Fc specific alkaline phosphatase conjugated secondary antibody (Sigma A-7434), diluted 1:2000 in Milk/PBSTS. After washing again as above, the reaction was developed with p-nitrophenyl phosphate disodium substrate (Sigma 104-105) and the absorbance at 405 nm read at intervals.

The results were normalized by staining with sulforhodamine B (SRB Sigma S 1402) to determine cell numbers. The alkaline phosphatase substrate was removed from the wells and the cells washed with PBS. The plates were then incubated with 0.4% SRB in 1% acetic acid for 30 minutes (200 μl/well), rinsed 4 times in 1% acetic acid, blotted dry and then 200 μl/well of 10 mM Tris pH 10.5 added. After mixing, the absorbance at 570 nm was read.

Neutral Red/Crystal Violet Staining of Foci

The survival of transfected cells in the absence or presence of G418 was monitored by staining of foci/clones with neutral red in vivo with subsequent crystal violet staining. The medium was removed from the cells and replaced with fresh medium containing 0.0025% neutral red (Sigma N2889) and the cells incubated for 3 hours at 37° C. Cells were washed twice with PBS, fixed in 3.5% formaldehyde for 15 minutes, washed twice again in PBS and then with distilled water and the number of (live) foci counted. The cells could then be re-stained with crystal violet by incubating with an 0.1% crystal violet (Sigma C0775) solution in 20% methanol for 20 minutes at room temperature, followed by 3 washes in 20% methanol and a wash with distilled water.

Preparation of Cells Cured of Endogenous Replicon

Replicon enhanced cells designated 10IFN and C1.60/cu were produced using different HCV inhibitory agents. Based on the techniques described herein additional replicon enhanced clones can readily be obtained.

10IFN was obtained by curing a Huh-7 cell of a replicon using human IFN-α2b. Huh-7 cells containing HCV replicons (designated HBI10, HBIII4, HBIII27 and HBIII18) were cultured for 11 days in the presence of 100 U/ml recombinant human IFN-α2b (Intron-A, Schering-Plough), and subsequently for 4 days in the absence of IFN-α2b. At several time points during this period, the clones were analyzed for the presence of HCV proteins and RNA by Western and Northern blotting. After 7 days of incubation with IFN-α2b, HCV proteins could no longer be detected in any of these clones by Western blotting and similar effects were seen with RNA signals in Northern blots. IFN-α2b treated cells were stored in liquid nitrogen until used for transfection experiments.

C1.60/cu was obtained by curing a Huh-7 cell of a replicon using an HCV inhibitory compound. The presence of HCV RNA was determined using PCR (TaqMan) at 4, 9, 12 and 15 days. From day 9 the amount of HCV RNA was below the limit of detection. To further test the disappearance of the replicon, 4 million cells of cured Clone 60 cells (after the 15 days of treatment) were plated in the presence of 1 mg/ml G418. No viable cells were observed, confirming that absence of HCV replicons able to confer G418 resistance.

Example 2

Selection and Characterization of Cell Clones Containing Functional HCV Replicons Huh-7 cells ($2-8\times10^6$) were transfected by electroporation with in vitro transcribed replicon RNAs (10-20 µg), plated at a density ranging from $2.5\times10^3$ to $10\times10^3/cm^2$, and cultured in the presence of 0.8-1 mg/ml G418. The majority of replicon transfected cells became transiently resistant to G418 and duplicated normally for 7 to 12 days in the presence of the drug, while cells transfected with irrelevant RNAs and mock transfected cells did not survive more than 7 days (data not shown). Transient resistance to G418 was likely due to persistence of the Neo protein expressed from the transfected RNA, since it was observed also with mutated replicons unable to replicate. Approximately 2 weeks after transfection, transient resistance declined, most cells died and small colonies of cells permanently resistant to the antibiotic became visible in samples transfected with HCVNeo.17 RNA, but not in cells transfected with other replicon RNAs.

In several experiments, the frequency of G418 resistant clones ranged between 10 and 100 clones per $10^6$ transfected cells. About 20 G418 resistant colonies were isolated, expanded and molecularly characterized. PCR and RT-PCR analysis of nucleic acids indicated that all clones contained HCV RNA but not HCV DNA, demonstrating that G418 resistance was due to the presence of functional replicons (data not shown). This result was confirmed by Northern blot analysis and metabolic labeling with 3H-uridine, which revealed the presence of both genomic and antigenomic HCV RNAs of the expected size (data not shown). Lastly, western blot, immunoprecipitation and immunofluorescence experiments showed that these clones expressed all HCV non-structural proteins as well as Neo protein (data not shown).

Clones differed in terms of cell morphology and growth rate. Replicon RNA copy number (500-10000 molecules/cell) and viral protein expression also varied between different clones (data not shown). However, the amount of replicon RNA and proteins also varied with passages and with culture conditions and was higher when cells were not allowed to reach confluency, suggesting that replicons replicated more efficiently in dividing cells than in resting cells. Processing of the viral polyprotein occurred with kinetics similar to those observed in transfected cells.

Interestingly, in all tested clones HCV replication was efficiently inhibited by treating the cells with IFN-α2b. The $EC_{50}$ was between 1 and 10 U/ml, depending on the clone.

Example 3

Identification of Adaptive Mutations

The low number of G418 resistant clones derived from HCVNeo.17 RNA transfection suggested that replication could require mutation(s) capable of adapting the replicon to the host cell (adaptive mutations) and/or that only a small percentage of Huh-7 cells were competent for HCV replication. To verify the first hypothesis, mutations in replicons RNAs derived from selected cell clones were identified.

RNA sequences for different replicons were determined using standard techniques. Such techniques involved isolating RNA from several independent clones, reverse transcription to produce cDNA, amplifying cDNAs by PCR and cloning into an appropriate vector. The cDNA spanning almost the entire HCV NS region (126 bp at the 3' end of the EMCV IRES and 5650 bp of the HCV NS region (i.e., the entire NS ORF and 298 nucleotides at the 3' end) from 5 clones (HBI10, HBIII12, HBIII8, HBIII27, HBIV1) were recloned and sequenced. In addition, the NS5A coding region (nt. 4784-6162) from 3 additional clones (HB 77, HB 68 and HB 60) were recloned and sequenced.

To discriminate mutations present in the replicon RNA from those derived from the cloning procedure, at least 2 isolates derived from independent RT-PCR experiments were sequenced for each cell clone. Comparison of the nucleotide sequences with the parental sequence indicated that each isolate contained several mutations (Tables 4A and 4B).

TABLE 4A

| | HBIII 12 | | HBIII 18 | | HBI 10 | | HBIII 27 | |
|---|---|---|---|---|---|---|---|---|
| Cell clone isolate | 4 1674-7460 | 29 1674-7460 | 28 1674-7460 | 61 1674-7460 | 12 1674-7460 | 43 1674-7460 | 13 1674-7460 | 72 1674-7460 |
| EMCV IRES 126 bp | A @ 1736 | A @ 1736 | | C 1752 T | | | | T 1678 C |
| NS3 1895 bp | G 2009 C | A 2330 G | T 2150 C | T 2015 C | T 1811 A | A 2330 G | G 2009 C | G 2009 C |
| | A 2698 G | C 2505 T | C 2196 A | A 2338 G | A 2330 G | A 2882 G | T 2015 C | C 2052 A |
| | G 2764 A | G 2764 A | T 3023 A | C 2616 T | T 2666 C | T 3673 C | C 2336 G | G 2644 A |
| | A 3256 G | T 3085 C | T 3134 C | A 2664 G | T 3395 C | | A 3130 T | C 2803 A |
| | T 3273 C | | C 3267 T | A 3148 G | | | A 3401 G | T 2823 A |
| | | | | T 3286 C | | | A 3518 C | T 3692 C |
| | | | | C 3615 T | | | | |
| | | | | C 3657 T | | | | |

TABLE 4A-continued

| | HBIII 12 | | HBIII 18 | | HBI 10 | | HBIII 27 | |
|---|---|---|---|---|---|---|---|---|
| Cell clone isolate | 4 1674-7460 | 29 1674-7460 | 28 1674-7460 | 61 1674-7460 | 12 1674-7460 | 43 1674-7460 | 13 1674-7460 | 72 1674-7460 |
| NS4A 161 bp | T 3790 C | | A 3847 G | T 3827 A | T 3742 C | | A 3743 G | A 3797 G |
| NS4B 782 bp | T 3869 C *A 4107 G* *T 4185 C* A 4428 G | C 4283 T *C 4429 T* | G 4300 A | A 4136 G A 4261 G G 4309 A *A 4449 G* | *T 4290 C* | *A 4053 G* *A 2496 C* T 4316 G | G 3880 A *T 4200 C* A 4366 G | C 4547T |
| NS5A 1340 bp | A 4847 C G 5158 A *G 5175 C* C 5243 T C 5390 T A 5719 G | *G 4728 A* *A 4845 G* C 5243 T G5512T A 5521 G A 5600 G A 5740 C | C 5243 T A 5486 G C 5596 T *G 5823 A* | *C 4729 A* T 4993 C G 5095 A *T 5334 C* A 5374 T *T 5379 A* T 5480 C A 5513 G T 5977 C | A 4694 T AAA @ 4842 T 5237 C | A 4675 G *A 4761 G* AAA @ 4842 T 5368 C | A 4855 G C 5006 T T 5318 C *A 5574 G* G 5866 A | A 4888 G C 4985 T T 5030 A T 5090 A T 5318 C *A 5328 G* *A 5399 G* *A 5574 G* |
| NS5B 1477 bp | T 6316 C T 6589 C T 7370 C | A 6406 G *G 6756 A* *G 6963 T* | T 6074 C A 6541 G *A 6732 G* *A 7350 T* *A 7359 G* | *A 6150 G* A 6218 G T 7352 A | A 6911 G | A 5986 G *T 6099 C* *C 6141 T* G 6463 A *C 6849 T* T 6865 C | G 6479 C *C 6870 T* A 7213 G T 7448 C | *G 6156 A* *G 7434 A* T 7444 C |

Clone name and isolate number are indicated in the first and second row, respectively.
The first and the last nucleotide of the region that was recloned and sequenced are indicated in the third row.
Nucleotide (IUB code) substitutions are indicated with the original nucleotide, its position and mutated nucleotide.
Nucleotide(s) insertions are indicated with the nucleotide(s), the symbol @ and the position of the nucleotide preceding insertion.
Numbering refers to the first nucleotide of the replicon sequence (EMBL-genbank No. AJ242652).
The region in which mutations are located and the nucleotide length of each region are indicated in the left most column.
Silent mutations are in italic.
Non sense mutations are underlined.
Consensus mutations are bold.

TABLE 4B

| | Cell clone | | | | | | | |
|---|---|---|---|---|---|---|---|---|
| | HBIV 1 | | HB 77 | | HB 68 | | HB 60 | |
| | isolate | | | | | | | |
| | 85 1674-7460 | 93 1674-7460 | 10 4784-6162 | 14 4465-6162 | 42 4784-6162 | 1 4465-6162 | 13 4784-6162 | 7 4784-6162 |
| EMCV IRES 126 bp | | A @ 1736 | | | | | | |
| NS3 1895 bp | A 3403 G | A 2572 G A 3454 G | | | | | | |
| NS4A 161 bp | | | | | | | | |
| NS4B 782 bp | A 4084 G | C 3892 T | | | | | | |
| NS5A 1340 bp | T 4742 C C 5315 T G 5431 T T 5751 C T 5797 C | A 4847 C A 5225 G C 5315 T G 5320 A T 5356 A G 5523 A T 5888 A | C 4813 T G 5060 C C 5337 A | A 4699 C A 5161 G C 5337 A A 5459 G T 5977 C | T 5171 G C 5298 T C 5337 A A 5639 G A 5969 G | T 4587 C T 4972 C A 5094 G A 5278 G G 5320 A C 5532 T | A 4821 G G 5320 A A 5414 G T 5601 G C 5808 T | C 5337 G C 5551 T G 5806 A |
| NS5B 1477 bp | T 6144 A A 6365 G A 6656 G A 6677 G T 6855 C T 6947 A T 6997 C G 7041 T A 7187 C | T 6855 C A 7135 G T 7171 C | | | | | | |

See Table 4A legend.

The frequency of mutations ranged between $1.7 \times 10^{-3}$ and $4.5 \times 10^{-3}$ (average $3 \times 10^{-3}$). The majority of mutations were nucleotide substitutions, although insertions of 1 or more nucleotides were also observed (Tables 4A and 4B).

Approximately 85% of the mutations found only in 1 isolate (non-consensus) were randomly distributed in the recloned fragment, and possibly include mis-incorporation during the PCR amplifications. Conversely, the remaining 15% of the mutations were common to 2 or more isolates derived from independent RT-PCR experiments (consensus mutations), and presumably reflected mutations present in the template RNA.

Consensus mutations were found in all isolates and were either common to isolates derived from the same clone (consensus A), or to isolates derived from different clones (consensus B). Analysis of additional isolates derived from the same cell clones indicated that consensus A mutations were not always present in all isolates derived from one clone (data not shown). This observation, together with the presence of consensus B mutations, suggests that, even within a single cell clone, replicons exist as quasi-species of molecules with different sequences.

At variance with non-consensus mutations, consensus mutations were not randomly distributed but were clustered in the regions coding for the NS5A protein (frequency $1 \times 10^{-3}$) and for the NS3 protein (frequency $0.5 \times 10^{-3}$). Only one consensus mutation was found in the region coding for the NS5B protein (frequency $0.1 \times 10^{-3}$ nucleotides) and none in the regions coding for NS4A and NS4B. Interestingly, 1 consensus mutation was observed also in the EMCV IRES.

With the exception of 2 silent mutations found in NS5A and NS5B, consensus mutations occurring in the NS region resulted in changes in the deduced amino acid sequence (Tables 5A and 5B). Noticeably, these amino acid changes occurred in residues that are conserved in all or most natural HCV isolates. Interestingly, clones HB 77 and HB 60 displayed different nucleotide substitutions (C5337A and C5337G, respectively) resulting in the same amino acidic mutation (S 2204 R).

Example 4

Functional Characterization of Consensus Mutations

The identification of consensus mutations in recloned replicons indicated that replication proficiency of replicon RNAs contained in selected cell clones depended from the presence of such mutations. To substantiate this hypothesis, the effect of several consensus mutations on replication were analyzed.

Consensus mutations found in the NS5A region were more closely analyzed. Consensus mutations were segregated from the non-consensus ones, and pHCVNeo.17 derivatives containing single or multiple consensus mutations were constructed (Table 6).

TABLE 6

| Construct | Consensus mutations | | | G418 cfu/$10^5$ transfected cells |
|---|---|---|---|---|
| | NS3 | NS5A | EMCV IRES | |
| pHCVNeo17.wt | | | | 0-3 |
| pHCVNeo17.GAA | | | | 0 |
| pHCVNeo17.m0 | | S2204R | | 30-130 |
| pHCVNeo17.m1 | | N2041T | | 0-3 |
| pHCVNeo17.m2 | | S2173F | | 15-60 |
| pHCVNeo17.m3 | | S2197F | | 160-500 |
| pHCVNeo17.m4 | | L2198S | | 30-50 |
| pHCVNeo17.m5 | | K@2039 | | 25-55 |
| pHCVNeo17.m6 | E1202G; A1347T | S2173F | Extra A | 13-100 |
| pHCVNeo17.m7 | | N2041T; S2173F | | 0-1 |
| pHCVNeo17.m8 | | N2041T; S2197F | | 360-500 |
| pHCVNeo17.m9 | | N2041T; L2198S | | 140-170 |
| pHCVNeo17.m10 | E1202G | K@2039 | | 1060 |
| pHCVNeo17.m11 | | S2197F; A2199T | | 900 |
| pHCVNeo17.m12 | | N2041T; S2197F; A2199T | | >1000 |

TABLE 5A

| Cell clone | HBIII 12 | | HBLII 18 | | HBI 10 | | HBIII 27 | |
|---|---|---|---|---|---|---|---|---|
| isolate | 4 | 29 | 28 | 61 | 12 | 43 | 13 | 72 |
| NS3 | G 1095 A A 1347 T | E 1202 G A 1347 T | | | E 1202 G | E 1202 G | G 1095 A | G 1095 A |
| NS4A | | | | | | | | |
| NS4B | | | | | | | | |
| NS5A | N 2041 T S 2173 F | S 2173 F | S 2173 F | E 2263 | K @ 2039 | K @ 2039 | L 2198 S R 2283 R | L 2198 S R 2283 R |
| NS5B | | | | | | | | |

See Table 4A legend.

TABLE 5B

| Cell clone | HBIV 1 | | HB 77 | | HB 68 | | HB 60 | |
|---|---|---|---|---|---|---|---|---|
| isolate | 85 | 93 | 10 | 14 | 42 | 1 | 13 | 7 |
| NS3 | | | | | | | | |
| NS4A | | | | | | | | |
| NS4B | | | | | | | | |
| NS5A | S 2197 F | N 2041 T S 2197 F A 2199 T | S 2204 R | S 2204 R | S 2204 R | A 2199 T | A 2199 T | S 2204 R |
| NS5B | | N 2710 N | N 2710 N | | | | | |

See Table 4A legend.

TABLE 6-continued

| Construct | Consensus mutations | | EMCV IRES | G418 cfu/$10^5$ transfected cells |
|---|---|---|---|---|
| | NS3 | NS5A | | |
| pHCVNeo17.m13 | | N2041T; S2197F | Extra A | 100 |
| pHCVNeo17.m14 | | S2197F; A2199T | Extra A | >500 |
| pHCVNeo17.m15 | | A2199T | | 300-600 |

Huh-7 cells (2 × $10^6$) were transfected with 10 µg of RNA transcribed from the indicated constructs.
Approximately 2 × $10^5$ cells were plated in a 10 cm tissue culture dish and cultured with 1 mg/ml G418 for 20 days.
Colonies surviving selection were stained with crystal violet and counted.

RNAs transcribed in vitro from these constructs were transfected in Huh-7 cells and the affect on replication was estimated by counting neomycin resistant colonies (G418 cfu). As shown in Table 6, all but 1 construct containing single consensus mutations showed a significant increase on G418 cfu efficiency, thus indicating that the corresponding mutations improved replication. Noticeably, 2 mutants containing single mutations in NS5A (m3 and m15) were clearly more effective than all other single mutants. Results of mutants containing 2 or more mutations, indicated the presence of a synergistic effect in some combinations (m8, m9, m11 and possibly m10), but also a slightly antagonistic effect in 1 mutant (m7).

Example 5

Replicon Replication in the Absence of Selection

Replication of HCV replicons in the absence of a G418 selection was detected using quantitative PCR (TaqMan). At 24 hours post-transfection a large amount of replicon RNA was detected in cells transfected with all replicons, including the GAA control replicon containing mutations in the catalytic GDD motif of the NS5B polymerase. This result suggested that analysis at very early time points (up to 48 hour post-transfection) essentially measured the input RNA. Northern blot analysis also indicated that after 24 hours the majority of the transfected RNA was degraded intracellularly (data not shown).

Analysis at later time points showed that the amount of replicon RNA was considerably reduced at 4 days and eventually became undetectable (6/8 days) in cells transfected with replicon HCVNeo17.wt, but was still high in cells transfected with replicons m0, m3 and m15 (Table 7). At day six, that the amount of replicon RNA became undetectable in cells transfected with replicon HCVNeo17.wt, m0, and m2, but was detectable in cells transfected with replicon m3 and m15 (Table 7).

TABLE 7

| | Hu H7 | |
|---|---|---|
| Name | RNA equ. day 4 | RNA equ. day 6 |
| Wt | 1 x | 1 x |
| hcvneo17.m0 | 3 x | 1 x |
| hcvneo17.m2 | 1 x | 1 x |
| hcvneo17.m3 | 5 x | 3 x |
| hcvneo17.m15 | 6 x | 5 x |

Persistence of m0, m3 and m15 replicons RNA was abolished by treatment with interferon-α or with an HCV inhibitory compound (data not shown). Moreover, RNA persistence was not observed with mutated replicons carrying the NS5B GAA mutation besides adaptive mutations (data not shown). Taken together, these results demonstrated that quantitative PCR could be used to monitor replication at early times post-transfection, and can be used to evaluate the replication proficiency of replicon RNAs containing mutations.

Comparison of the results shown in Tables 6 and 7, indicated that there was a good correlation between the amount of replicon RNA detected by TaqMan and the G418 cfu efficiency. Nonetheless, some mutants (m2, m3) showed a pronounced effect on G418 cfu efficiency, and little if any effect on early replication as measured by TaqMan PCR, while other mutants (m0) showed the reverse behavior.

Example 6

HCV Replicon Enhanced Cells

HCV replicon enhanced cells were produced by introducing an HCV replicon into a host, then curing the host of the replicon. Adaptive mutations (or combinations of them) by themselves increased up to 2 orders of magnitude the G418 cfu efficiency and enhanced early replication comparably. Nonetheless, even with the most effective mutants, only a small percentage of transfected cells (<5%, data not shown) gave rise to G418 resistant clones containing functional replicons. This observation was attributed, at least in part to a low cloning efficiency of Huh-7 cells (data not shown), and only a fraction of Huh-7 cells being competent for replication.

Several clones were cured of endogenous replicons by treating them for about 2 weeks with IFN-α or with a HCV inhibitory compound. Analysis at the end of the treatment showed that neither viral proteins nor replicon RNA could be detected.

Cured cells (10IFN and Cl.60/cu) were transfected with mutated replicons and replication efficiency was determined by counting neomycin resistant clones (10IFN) or by TaqMan (10IFN and Cl.60/cu). As shown in Table 8, for all tested replicons the G418 cfu efficiency in 10IFN cells was at least 5 fold higher than in parental Huh-7 cells. This increase in G418 cfu efficiency was particularly relevant for a subset of mutants (m3, m5, m8, m9, m15).

TABLE 8

| Construct | Consensus mutations | | EMCV IRES | G418 cfu/$10^5$ transfected cells |
|---|---|---|---|---|
| | NS3 | NS5A | | |
| pHCVNeo17.wt | | | | 12-56 |
| pHCVNeo17.GAA | | | | 0 |
| pHCVNeo17.m0 | | S2204R | | 180-1000 |
| pHCVNeo17.m1 | | N2041T | | 8-13 |
| pHCVNeo17.m2 | | S2173F | | 2000 |
| pHCVNeo17.m3 | | S2197F | | 1600-3000 |
| pHCVNeo17.m4 | | L2198S | | 190-650 |
| pHCVNeo17.m5 | | K@2039 | | 1600-3000 |
| pHCVNeo17.m6 | E1202G; A1347T | S2173F | extra A | 600-2000 |
| pHCVNeo17.m7 | | N2041T; S2173F | | 170-800 |
| pHCVNeo17.m8 | | N2041T; S2197F | | >4000 |
| pHCVNeo17.m9 | | N2041T; L2198S | | 1400-3000 |
| pHCVNeo17.m10 | E1202G | K@2039 | | >4000 |
| pHCVNeo17.m11 | | S2197F; A2199T | | >4000 |

TABLE 8-continued

| Construct | Consensus mutations | | EMCV IRES | G418 cfu/10$^5$ transfected cells |
|---|---|---|---|---|
| | NS3 | NS5A | | |
| pHCVNeo17.m12 | | N2041T; S2197F; A2199T | | >4000 |
| pHCVNeo17.m13 | | N2041T; S2197F | extra A | >4000 |
| pHCVNeo17.m14 | | S2197F; A2199T | extra A | >4000 |
| pHCVNeo17.m15 | | A2199T | | >4000 |

10IFN cells (2 × 10$^6$) were transfected with 10 μg of RNA transcribed from the indicated constructs.
Approximately 2 × 10$^5$ cells were plated in a 10 cm tissue culture dish and cultured with 1 mg/ml G418 for 20 days.
Colonies surviving selection were stained with crystal violet and counted.

Strikingly, the best mutants yielded a number of G418 resistant clones ranging between 20 and 80% of the cell clones which grew in the absence of G418 (data not shown), thus indicating that the majority of 10IFN cells were competent for replication. This result was confirmed by TaqMan analysis (Table 9), in which the fold increase versus the parental Huh-7 cells was very high. The data indicates that replicons carrying adaptive mutations replicate vigorously in replicon enhanced cells such as 10IFN and C1.60/cu.

TABLE 9

| | 10IFN | | C1.60/cu. | |
|---|---|---|---|---|
| Name | RNA equ. Day 4 | RNA equ. day 6 | RNA equ. day 4 | RNA equ. Day 6 |
| Wt | 1 x | 1 x | 1 x | 1 x |
| hcvneo17.m0 | 46 x | 12 x | 78 x | 512 x |
| hcvneo17.m2 | 2 x | 2 x | 1 x | 2 x |
| hcvneo17.m3 | 68 x | 49 x | 19 x | 392 x |
| hcvneo17.m15 | 247 x | 80 x | 268 x | 5518 x |

Expression of viral proteins was determined in replicon enhanced cells using an ELISA assay designed to detect the NS3 protein in transfected cells plated in 96 wells microtiter plates (Cell-ELISA). As shown in Table 10, 24 hours post-transfection cells transfected with all tested replicons expressed low but detectable levels of the NS3 protein.

TABLE 10

| | NS3 arbitrary units | | | |
|---|---|---|---|---|
| Name | h p.t. | | 96 h p.t. | |
| Construct | − | +IFN | − | +IFN |
| Mock | 1 | 1 | 1 | 1 |
| pHCVNeo17.wt | 3.7 | 4.2 | 1.2 | 1.3 |
| pHCVNeo17.GAA | 3.1 | 3.2 | 1.1 | 1 |
| pHCVNeo17.m0 | 3.4 | 3.2 | 9.9 | 0.8 |
| pHCVNeo17.m3 | 5.7 | 4.6 | 4.7 | 1.5 |
| pHCVNeo17.m8 | 6.6 | 5.1 | 15.1 | 1.4 |
| pHCVNeo17.m10 | 8 | 5.6 | 9.2 | 1.8 |
| pHCVNeo17.m11 | 8.4 | 6.2 | 13.6 | 1.8 |

10IFN cells (2 × 10$^6$) were transfected with 10 μg of RNA transcribed from the indicated constructs.
Cells were plated in 96 wells microtiter plates as indicated in Example 1.
Where indicated (+IFN), IFN-α (100 U/ml) was added to the culture medium 4 hours post-transfection.
At the indicated times post-transfection, cells were fixed and analyzed by Cell-ELISA.

The early expression shown in Table 10 is likely due to translation of transfected RNA, since it was comparable in all replicons (including that carrying the GAA mutation) and was not affected by IFN-α. At 4 days post-transfection, NS3 expression persisted or increased in cells transfected with replicons carrying consensus mutations, but could not be detected anymore in cells transfected with wt and GAA replicons. In addition, NS3 expression was almost completely abolished when cells were cultured in the presence of IFN-α.

Taken together, these results indicated that the level of NS3 expression reflected the replication rate. Indeed, NS3 expression level (Table 10) paralleled the RNA level measured by TaqMan (Table 9). The high replication proficiency of 10IFN cells was further confirmed by immunofluorescence experiments which showed that more than 50% of cells transfected with replicons m8 and m11 expressed high level of viral proteins, and that expression was almost completely abolished by IFN-α.

Example 7

Replication of Full Length Constructs

This example illustrates the ability of a full length HCV genome containing adaptive mutations described herein to replicate in a replicon enhanced host cell. The full length sequence of the HCV isolate Con-1 (EMBL-Genbank No. AJ238799) (plasmid pHCVRBFL.wt) and 2 derivatives containing either the N2041T and S2173 F mutations (plasmid pHCVRBFL.m8) or the S2197F and A2199T mutations (plasmid pHCVRBFL.m11) were used as starting constructs.

RNAs transcribed from the starting constructs were transfected in 10IFN cells and their replication proficiency was assessed by Cell-ELISA, immunofluorescence and TaqMan. Both constructs containing consensus mutations (pHCVRB-FL.m8 and pHCVRBFL.m11) replicated, while no sign of replication was observed with the wt. construct (data not shown).

Example 8

Replicons with Reporter Gene

This example illustrates an HCV replicon containing adaptive mutations and a reporter gene. A pHCVNeo17.wt derivative where the Neo coding region was substituted with that coding for human placental secretory alkaline phosphatase (pRBSEAP5.wt) and a derivative also containing the N2041T and S2173F mutations (plasmid pRBSEAP5.m8) were constructed. RNAs transcribed from these plasmids were transfected in 10IFN cells and their replication proficiency was assessed by measuring secretion of alkaline phosphatase. Analysis of the kinetics of secretion suggested that only plasmid pRBSEAP5.m8 was competent for replication (data not shown).

Example 9

SEQ. ID. Nos. 1 and 2

SEQ. ID. NOs. 1 and 2 are provided as follows:

SEQ. ID. NO. 1
MSTNPKPQRKTKRNTNRRPQDVKFPGGGQIVGGVYLLPRRGPRLGVRATR

KTSERSQPRGRRQPLPKARQPEGRAWAQPGYPWPLYGNEGLGWAGWLLSP

RGSRPSWGPTDPRRRSRNLGKVLDTLTCGFADLMGYIPLVGAPLGGAARA

-continued

LAHGVRVLEDGVNYATGNLPGCSFSIFLLALLSCLTIPASAYEVRNVSGV
YHVTNDCSNASIVYEAADMIMHTPGCVPCVRENNSSRCWVALTPTLAARN
ASVPTTTIRRHVDLLVGAAALCSAMYVGDLCGSVFLVAQLFTFSPRRHET
VQDCNCSIYPGHVTGHRMAWDMMMNWSPTAALVVSQLLRIPQAVVDMVAG
AHWGVLAGLAYYSMVGNWAKVLIVMLLFAGVDGGTYVTGGTMAKNTLGIT
SLFSPGSSQKIQLVNTNGSWHINRTALNCNDSLNTGELAALFYVHKFNSS
GCPERMASCSPIDAFAQGWGPITYNESHSSDQRPYCWHYAPRPCGIVPAA
QVCGPVYCFTPSPVVVGTTDRFGVPTYSWGENETDVLLLNNTRPPQGNWF
GCTWMNSTGFTKTCGGPPCNIGGIGNKTLTCPTDCFRKHPEATYTKCGSG
PWLTPRCLVHYPYRLWHYPCTVNFTIPKVRMYVGGVEHRLEAACNWTRGE
RCNLEDRDRSELSPLLLSTTEWQVLPCSFITLPALSTGLIHLHQNVVDVQ
YLYGIGSAVVSFAIKWEYVLLLFLLLADARVCACLWMMLLIAQAEAALEN
LVVLNAASVAGAHGILSFLVFFCAAWYIKGRLVPGAAYALYGVWPLLLLL
LALPPRAYAMDREMAASCGGAVFVGLILLTLSPHYKLFLARLLWWLQYFI
TRAEAHLQVWIPPLNVRGGRDAVILLTCAIHPELIFTITKILLAILGPLM
VLQAGITKVPYFVRAHGLIRACMLVRKVAGGHYVQMALMKLAALTGTYVY
DHLTPLRDWAHAGLRDLAVAVEPVVFSDMETKVITWGADTAACGDIILGL
PVSARRGREIHLGPADSLEGQGWRLLAPLTAYSQQTRGLLGCIITSLTGR
DRNQVEGEVQVVSTATQSFLATCVNGVCWTVYHGAGSKTLAGPKGPLTQM
YTNVDQDLVGWQAPPGARSLTPCTCGSSDLYLVTRHADVIPVRRRGDSRG
SLLSPRPVSYLKGSSGGPLLCPSGHAVGIFRAAVCTRGVAKAVDFVPVES
METTMRSPVFTDNSSPPAVPQTFQVAHLHAPTGSGKSTKVPAAYAAQGYK
VLVLNPSVAATLGFAYMSKAHGIDPNIRTGVRTITTGAPITYSTYGKFL
ADGGCSGGAYDIIICDECHSTDSTTILGIGTVLDQAETAGARLVVLATAT
PPGSVTVPHPNLEEVALSSTGELPFYGKAIPIETLKGGRHLIFCHSKKKC
DELAAKLSGLGLNAVAYYRGLDVSVIPTSGDVIVVATDALMTGFTGDFDS
VLDCNTCVTQTVDFSLDPTFTIFITTVPQDAVSRSQRRGRTGRGRMGIYR
FVTPGERPSGMFDSSVLCECYDAGCAWYELTPAETSVRLRAYLNTPGLPV
CQDHLEFWESVFTGLTHIDAHFLSQTKQAGDNFPYLVAYQATVCARAQAP
PPSWDQMWKCLIRLKPTLHGPTPLLYRLGAVQNEVTITTTHPITKYIMAC
MSADLEVVTSTWVLVGGVLAALAAYCLTTGSVVIVGRLILSGKPAIIPDR
EVLYREFDEMEECASHLPYIEQGMQLAEQFKQKAIGLLQTATKQAEAAAP
VVESKWRTLEAFWAKHMWNFISGIQYLAGLSTLPGNPAIASLMAFTASIT
SPLTTQHTLLFNILGGWVAAQLAPPSAASAFVGAGIAGAAVGSIGLGKVL
VDILAGYGAGVAGALVAFKVMSGEMPSTEDLVNLLPAILSPGALVVGVVC
AALLRRHVGPGEGAVQWMNRLIAFASRGNHVSPTHYVPESDAAARVTQIL
SSLTITQLLKRLHQWINEDCSTPGSGSWLRDVWDWICTVLTDFKTWLQSK
LLPRLPGVPFFSCQRGYKGVWRGDIMQTTCPCGAQITGHVKNGSMRIVG
PRTCSNTWHGTFPLNAYTTGPCTPSPAPNYSRALWRVAAEEYVEVTRVGD
FHYVTGMTTDNVKCPCQVPAPEFFTEVDGVRLHRYAPACKPLLREEVTFL
VGLNQYLVGSQLPCEPEPDVAVLTSMLTDPSHITAETAKRRLARGSPPSL

-continued

ASSSASQLSAPSLKATCTTRHDSPDADLIEANLLWRQEMGGNITRVESEN
KVVILDSFEPLQAEEDEREVSVPAEILRRSRKFPRAMPIWARPDYNPPLL
ESWKDPDYVPPVVHGCPLPPAKAPPIPPPRRKRTVVLSESTVSSALAELA
TKTFGSSESSAVDSGTATASPDQPSDDGDAGSDVESYSSMPPLEGEPGDP
DLSDGSWSTVSEEASEDVVCCSMSYTWTGALITPCAAEETKLPINALSNS
LLRHHNLVYAATTSRSASLRQKKVTFDRLQVLDDHYRDVLKEMKAKASTV
KAKLLSVEEACKLTPPHSARSKFGYGAKDVRNLSSKAVNIIRSVWKDLL
EDTETPIDTTIMAKNEVFCVQPEKGGRKPARLIVFPDLGVRVCEKMALYD
VVSTLPQAVMGSSYGFQYSPGQRVEFLVNAWKAKKCPMGFAYDTRCFDST
VTENDIRVEESIYQCCDLAPEARQAIRSLTERLYIGGPLTNSKGQNCGYR
RCRASGVLTTSCGNTLTCYLKAAAACRAAKLQDCTMLVCGDDLVVICESA
GTQEDEASLRAFTEAMTRYSAPPGDPPKPEYDLELITSCSSNVSVAHDAS
GKRVYYLTRDPTTTPLARAAWETARHTPVNSWLGNIIMYAPTLWARMILM
THFFSILLAQEQLEKALDCQLYGACYSLEPLDLPQIIQRLHGLSAFSLHS
YSPGEINRVASCLRKLGVPPLRVWRHRARSVRARLLSQGGRAATCGKYLF
NWAVRTKLKLTPIPAASQLDLSSWFVAGYSGGDIYHSLSRARPRWFMWCL
LLLSVGVGIYLLPNR

SEQ. ID. NO. 2:
gccagccccgattggggcgacactccaccatagatcactcccctgtga
ggaactactgtcttcacgcagaaagcgtctagccatggcgttagtatgag
tgtcgtgcagcctccaggaccccccctcccgggagagccatagtggtctg
cggaaccggtgagtacaccggaattgccaggacgacccgggtcctttcttg
gatcaacccgctcaatgcctggagatttgggcgtgcccccgcgagactgc
tagccgagtagtgttgggtcgcgaaaggccttgtggtactgcctgatagg
gtgcttgcgagtgccccgggaggtctcgtagaccgtgcaccatgagcacg
aatcctaaacctcaaagaaaaaccaaacgtaacaccaaccgccgcccaca
ggacgtcaagttcccgggcggtggtcagatcgtcggtggagtttacctgt
tgccgcgcaggggccccaggttgggtgtgcgcgcgactaggaagacttcc
gagcggtcgcaacctcgtggaaggcgacaacctatccccaaggctcgcca
gcccgagggtagggcctgggctcagcccgggtaccctggcccctctatg
gcaatgagggcttggggtgggcaggatggctcctgtcacccgtggctct
cggcctagttgggccccacggaccccggcgtaggtcgcgcaatttggg
taaggtcatcgataccctcacgtgcggcttcgccgatctcatgggtaca
ttccgctcgtcggcgccccctaggggggcgctgccagggccctggcgcat
ggcgtccgggttctggaggacggcgtgaactatgcaacagggaatctgcc
cggttgctccttttctatcttccttttggctttgctgtcctgtttgacca
tcccagcttccgcttatgaagtgcgcaacgtatccggagtgtaccatgtc
acgaacgactgctccaacgcaagcattgtgtatgaggcagcggacatgat
catgcataccccgggtgcgtgccctgcgttcgggagaacaactcctccc
gctgctgggtagcgctcactcccacgctcgcggccaggaacgctagcgtc
ccactacgacgatacgacgccatgtcgatttgctcgttggggcggctgc -continued tctctgctccgctatgtacgtgggagatctctgcggatctgttttcctcg
tcgcccagctgttcaccttctcgcctcgccggcacgagacagtacaggac
tgcaattgctcaatatatcccggccacgtgacaggtcaccgtatggcttg
ggatatgatgatgaactggtcacctacagcagccctagtggtatcgcagt
tactccggatcccacaagctgtcgtggatatggtggcgggggcccattgg
ggagtcctagcgggccttgcctactattccatggtggggaactgggctaa
ggttctgattgtgatgctactctttgccggcgUgacggggggaacctatgt
gacagggggggacgatggccaaaaacaccctcgggattacgtccctctttt
cacccgggtcatcccagaaaatccagcttgtaaacaccaacggcagctgg
cacatcaacaggactgccctgaactgcaatgactccctcaacactgggtt
ccttgctgcgctgttctacgtgcacaagttcaactcatctggatgcccag
agcgcatggccagctgcagccccatcgacgcgttcgctcaggggtggggg
cccatcacttacaatgagtcacacagctcggaccagaggccttattgttg
gcactacgcaccccggccgtgcggtatcgtacccgcggcgcaggtgtgtg
gtccagtgtactgcttcaccccaagccctgtcgtggtggggacgaccgac
cggttcggcgtccctacgtacagttggggggagaatgagacggacgtgct
gcttcttaacaacacgcggccgccgcaaggcaactggtttggctgtacat
ggatgaatagcactgggttcaccaagacgtgcgggggccccccgtgtaac
atcgggggatcggcaataaaaccttgacctgccccacggactgcttccg
gaagcacccgaggccacttacaccaagtgtggttcggggccttggttga
cacccagatgcttggtccactacccatacaggctttggcactaccctgc
actgtcaactttaccatcttcaaggttaggatgtacgtggggggagtgga
gcacaggctcgaagccgcatgcaattggactcgaggagagcgttgtaacc
tggaggacagggacagatcagagcttagcccgctgctgctgtctacaacg
gagtggcaggtattgccctgttccttcaccaccctaccggctctgtccac
tggtttgatccatctccatcagaacgtcgtggacgtacaatacctgtacg
gtatagggtcggcggttgtctcctttgcaatcaaatgggagtatgtcctg
ttgctcttccttcttctggcggacgcgcgcgtctgtgcctgcttgtggat
gatgctgctgatagctcaagctgaggccgccctagagaacctggtggtcc
tcaacgcggcatccgtggccggggcgcatggcattctctccttcctcgtg
ttcttctgtgctgcctggtacatcaagggcaggctggtccctggggcggc
atatgccctctacggcgtatggccgctactcctgctcctgctggcgttac
caccacgagcatacgccatggaccgggagatggcagcatcgtgcggaggc
gcggttttcgtaggtctgatactcttgaccttgtcaccgcactataagct
gttcctcgctaggctcatatggtggttacaatattttatcaccagggccg
aggcacacttgcaagtgtggatccccccctcaacgttcggggggggccgc
gatgccgtcatcctcctcacgtgcgcgatccacccagagctaatctttac
catcaccaaaatcttgctcgccatactcggtccactcatggtgctccagg
ctggtataaccaaagtgccgtacttcgtgcgcgcacacgggctcattcgt
gcatgcatgctggtgcggaaggttgctgggggtcattatgtccaaatggc -continued tctcatgaagttggccgcactgacaggtacgtacgtttatgaccatctca
ccccactgcgggactgggcccacgcgggcctacgagaccttgcggtggca
gttgagcccgtcgtcttctctgatatggagaccaaggttatcacctgggg
ggcagacaccgcggcgtgtggggacatcatcttgggcctgcccgtctccg
cccgcaggggagggagatacatctgggaccggcagacagccttgaaggg
caggggtggcgactcctcgcgcctattacggcctactcccaacagacgcg
aggcctacttggctgcatcatcactagcctcacaggccgggacaggaacc
aggtcgaggggaggtccaagtggtctccaccgcaacacaatctttcctg
gcgacctgcgtcaatggcgtgtgttggactgtctatcatggtgccggctc
aaagacccttgccggcccaaagggcccaatcacccaaatgtacaccaatg
tggaccaggacctcgtcggctggcaagcgcccccggggcgcgttccttg
acaccatgcacctgcggcagctcggacctttacttggtcacgaggcatgc
cgatgtcattccggtgcgccggcggggcgacagcaggggggagcctactct
cccccaggccgtctcctacttgaagggctcttcgggcggtccactgctc
tgccctcggggcacgctgtgggcatctttcgggctgccgtgtgcacccg
aggggttgcgaaggcggtggactttgtacccgtcgagtctatggaaacca
ctatgcggtccccggtcttcacggacaactcgtcccctccggccgtaccg
cagacattccaggtggcccatctacacgcccctactggtagcggcaagag
cactaaggtgccggctgcgtatgcagcccaagggtataaggtgcttgtcc
tgaacccgtccgtcgccgccaccctaggtttcggggcgtatatgtctaag
gcacatggtatcgaccctaacatcagaaccggggtaaggaccatcaccac
gggtgcccccatcacgtactccacctatggcaagtttcttgccgacggtg
gttgctctgggggcgcctatgacatcataatatgtgatgagtgccactca
actgactcgaccactatcctgggcatcggcacagtcctggaccaagcgga
gacggctggagcgcgactcgtcgtgctcgccaccgctacgcctcgggat
cggtcaccgtgccacatccaaacatcgaggaggtggctctgtccagcact
ggagaaatccccttttatggcaaagccatccccatcgagaccatcaaggg
ggggaggcacctcattttctgccattccaagaagaaatgtgatgagctcg
ccgcgaagctgtccggcctcggactcaatgctgtagcatattaccgggc
cttgatgtatccgtcataccaactagcggagacgtcattgtcgagcaacg
gacgctctaatgacgggctttaccggcgatttcgactcagtgatcgactg
caatacatgtgtcacccagacagtcgacttcagcctggacccgaccttca
ccattgagacgacgaccgtgccacaagacgcggtgtcacgctcgcagcgg
cgaggcaggactggtaggggcaggatgggcatttacaggtttgtgactcc
aggagaacggccctcgggcatgttcgattcctcggttctgtgcgagtgct
atgacgcgggctgtgcttggtacgagctcacgcccgccgagacctcagtt
aggttgcgggcttacctaaacacaccagggttgcccgtctgccaggacca
tctggagttctgggagagcgtcttt acaggcctcacccacatagacgccc
atttcttgtcccagactaagcaggcaggagacaacttcccctacctggta
gcataccaggctacggtgtgcgccagggctcaggctccacctccatcgtg
ggaccaaatgtggaagtgtctcatacggctaaagcctacgctgcacgggc -continued caacgcccctgctgtataggctgggagccgttcaaaacgaggttactacc
acacaccccataaccaaatacatcatggcatgcatgtcggctgacctgga
ggtcgtcacgagcacctgggtgctggtaggcggagtcctagcagctctgg
ccgcgtattgcctgacaacaggcagcgtggtcattgtgggcaggatcatc
ttgtccggaaagccggccatcattcccgacagggaagtcctttaccggga
gttcgatgagatggaagagtgcgcctcacacctcccttacatcgaacagg
gaatgcagctcgccgaacaattcaaacagaaggcaatcgggttgctgcaa
acagccaccaagcaagcggaggctgctgctcccgtggtggaatccaagtg
gcggaccctcgaagccttctgggcgaagcatatgtggaatttcatcagcg
ggatacaatatttgcaggcttgtccactctgcctggcaaccccgcgata
gcatcactgatggcattcacagcctctatcaccagcccgctcaccaccca
acatacccccctgtttaacatcctgggggatgggtggccgcccaacttg
ctcctcccagcgctgcttctgctttcgtaggcgccggcatcgctggagcg
gctgttggcagcataggccttgggaaggtgcttgtggatattttggcagg
ttatggagcaggggtggcaggcgcgctcgtggcctttaaggtcatgagcg
gcgagatgccctccaccgaggacctggttaacctactccctgctatcctc
tcccctggcgccctagtcgtcggggtcgtgtgcgcagcgatactgcgtcg
gcacgtgggcccaggggagggggctgtgcagtggatgaaccggctgatag
cgttcgcttcgcggggtaaccacgtctcccccacgcactatgtgcctgag
agcgacgctgcagcacgtgtcactcagatcctctctagtcttaccatcac
tcagctgctgaagaggcttcaccagtggatcaacgaggactgctccacgc
catgctccggctcgtggctaagagatgtttgggattggatatgcacggtg
ttgactgatttcaagacctggctccagtccaagctcctgccgcgattgcc
gggagtcccttcttctcatgtcaacgtgggtacaagggagtctggcggg
gcgacggcatcatgcaaaccacctgcccatgtggagcacagatcaccgga
catgtgaaaaacggttccatgaggatcgtggggcctaggacctgtagtaa
cacgtggcatggaacattccccattaacgcgtacaccacgggcccctgca
cgccctccccggcgccaaattattctagggcgctgtggcgggtggctgct
gaggagtacgtggaggttacgcgggtgggggatttccactacgtgacggg
catgaccactgacaacgtaaagtgccgtgtcaggttccggcccccgaat
tcttcacagaagtggatggggtgcggttgcacaggtacgctccagcgtgc
aaacccctcctacgggaggaggtcacattcctggtcgggctcaatcaata
cctggttgggtcacagctcccatgcgagcccgaaccggacgtagcagtgc
tcacttccatgctcaccgaccccctcccacattacggcggagacggctaag
cgtaggctggccaggggatctcccccctccttggccagctcatcagctag
ccagctgtctgcgccttccttgaaggcaacatgcactacccgtcatgact
ccccggacgctgacctcatcgaggccaacctcctgtggcggcaggagatg
ggcgggaacatcacccgcgtggagtcagaaaataaggtagtaattttgga
ctctttcgagccgctccaagcggaggaggatgagagggaagtatccgttc
cggcggagatcctgcggaggtccaggaaattccctcgagcgatgcccata -continued tgggcacgcccggattacaaccctccactgttagagtcctggaaggaccc
ggactacgtccctccagtggtacacgggtgtccattgccgcctgccaagg
cccctccgataccacctccacggaggaagaggacggttgtcctgtcagaa
tctaccgtgtcttctgccttggcggagctcgccacaaagaccttcggcag
ctccgaatcgtcggccgtcgacagcggcacggcaacggcctctcctgacc
agccctccgacgacggcgacgcgggatccgacgttgagtcgtactcctcc
atgcccccccttgaggggagccggggatcccgatctcagcgacgggtc
ttggtctaccgtaagcgaggaggctagtgaggacgtcgtctgctgctcga
tgtcctacacatggacaggcgccctgatcacgccatgcgctgcggaggaa
accaagctgcccatcaatgcactgagcaactcttgctccgtcaccacaa
cttggtctatgctacaacatctcgcagcgcaagcctgcggcagaagaagg
tcacctttgacagactgcaggtcctggacgaccactaccgggacgtgctc
aaggagatgaaggcgaaggcgtccacagttaaggctaaacttctatccgt
ggaggaagcctgtaagctgacgcccccacattcggccagatctaaatttg
gctatggggcaaaggacgtccggaacctatccgcaaggccgttaaccac
atccgctccgtgtggaaggacttgctggaagacactgagacaccaattga
caccaccatcatgcaaaaaatgaggttttctgcgtccaaccagagaagg
ggggccgcaagccagctcgccttatcgtattcccagatttgggggttcgt
gtgtgcgagaaaatggccctttacgatgtggtctccaccctccctcaggc
cgtgatgggctcttcatacggattccaatactctcctggacagcgggtcg
agttcctggtgaatgcctggaaagcgaagaaatgccctatgggcttcgca
tatgacacccgctgttttgactcaacggtcactgagaatgacatccgtgt
tgaggagtcaatctaccaatgttgtgacttggccccgaagccagacagg
ccataaggtcgctcacagagcggctttacatcgggggcccctgactaat
tctaaagggcagaactgcggctatcgccggtgccgcgcgagcggtgtact
gacgaccagctgcggtaatacctcacatgttacttgaaggccgctgcgg
cctgtcagctgcgaagctccaggactgcacgatgctcgtatgcggagac
gaccttgtcgttatctgtgaaagcgcggggacccaagaggacgaggcgag
cctacgggccttcacggaggctatgactagatactctgcccccctgggg
acccgcccaaaccagaatacgacttggagttgataacatcatgctcctcc
aatgtgtcagtcgcgcacgatgcatctggcaaaagggtgtactatctcac
ccgtgaccccaccaccccccttgcgcgggctgcgtgggagacagctagac
acactccagtcaattcctggctaggcaacatcatcatgtatgcgcccacc
ttgtgggcaaggatgatcctgatgactcatttcttctccatccttctagc
tcaggaacaacttgaaaaagccctagattgtcagatctacggggcctgtt
actccattgagccacttgacctacctcagatcattcaacgactccatggc
cttagcgcattttcactccatagttactctccaggtgagatcaataggt
ggcttcatgcctcaggaaacttggggtaccgcccttgcgagtctggagac
atcgggccagaagtgtccgcgctaggctactgtcccagggggggagggct
gccacttgtggcaagtacctcttcaactgggcagtaaggaccaagctcaa
actcactccaatcccggctgcgtcccagttggatttatccagctggttcg

```
ttgctggttacagcgggggagacatatatcacagcctgtctcgtgcccga
ccccgctggttcatgtggtgcctactcctactttctgtaggggtaggcat
ctatctactccccaaccgatgaacggggagctaaacactccaggccaata
ggccatcctgtttttttccctttttttttttctttttttttttttttttt
ttttttttttttttttctcctttttttttcctctttttttcctttctttt cctttggtggctccatcttagccctagtcacggctagctgtgaaaggtcc
gtgagccgcttgactgcagagagtgctgatactggcctctctgcagatca
agt
```

Other embodiments are within the following claims. While several embodiments have been shown and described, various modifications may be made without departing from the spirit and scope of the present invention.

What is claimed is:

1. An isolated nucleic acid molecule comprising an HCV NS5A region that encodes the NS5A region of SEQ ID NO: 1, wherein the encoded NS5A region is altered by one or more mutations selected from the group consisting of:
   a) amino acid 2041 being Thr,
   b) a Lys insertion between amino acid residues 2039 and 2040,
   c) amino acid 2173 being Phe,
   d) amino acid 2197 being Phe,
   e) amino acid 2198 being Ser, and
   f) amino acid 2204 being Arg,
   wherein the encoded NS5A region further comprises a Thr at position 2199 and wherein the HCV replicon comprising the mutated NS5A region has increased replication as compared to an HCV replicon comprising an NS5A region without the mutations.

2. An isolated nucleic acid molecule comprising nucleotides 1-7989 of SEQ ID NO. 3, or the RNA version thereof, wherein the nucleotides of SEQ ID NO: 3 have been altered by one or more mutations selected from the group consisting of:
   a) nucleotides 5314-5316 modified to code for phenylalanine and nucleotides 5320-5322 modified to code for threonine;
   b) nucleotides 4846-4848 modified to code for threonine, nucleotides 5314-5316 modified to code for phenylalanine, and nucleotides 5320-5322 modified to code for threonine; and
   c) nucleotides 5314-5316 modified to code for phenylalanine, nucleotides 5320-5322 modified to code for threonine, and an extra adenosine inserted after nucleotide 1736;
   wherein an HCV replicon comprising said one or more mutations has increased replication as compared to an HCV replicon without said mutations.

3. An expression vector comprising the nucleic acid molecule of claim 2, wherein said nucleotides are transcriptionally coupled to an exogenous promoter.

4. A recombinant human hepatoma cell, wherein said cell comprises the nucleic acid of claim 2 and said cell is either Huh-7 or is derived from Huh -7.

5. The recombinant cell of claim 4, wherein said hepatoma cell is an Huh-7 cell.

6. The recombinant cell of claim 4, wherein said cell is derived from a Huh-7 cell.

* * * * *